US010022555B2

(12) United States Patent
Tapper et al.

(10) Patent No.: US 10,022,555 B2
(45) Date of Patent: *Jul. 17, 2018

(54) LIGHT THERAPY BANDAGE SYSTEM

(71) Applicant: Johnson & Johnson Consumer Inc., Skillman, NJ (US)

(72) Inventors: Jay Tapper, Wayne, PA (US); David Shuter, Palm Beach Gardens, FL (US); Charles Peter Althoff, New York, NY (US); Jeff Michaelson, Huntington Woods, MI (US); Bradley Feild Craddock, Brooklyn, NY (US); Lulin Ding, Brooklyn, NY (US); Marc-Aurelian Vivant, New York, NY (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/747,687

(22) Filed: Jun. 23, 2015

(65) Prior Publication Data
US 2015/0290470 A1 Oct. 15, 2015

Related U.S. Application Data

(60) Continuation-in-part of application No. 14/212,601, filed on Mar. 14, 2014, and a continuation-in-part of
(Continued)

(51) Int. Cl.
*A61B 5/06* (2006.01)
*A61N 5/06* (2006.01)
(Continued)

(52) U.S. Cl.
CPC .. *A61N 5/0616* (2013.01); *A61B 2017/00057* (2013.01); *A61B 2017/00084* (2013.01);
(Continued)

(58) Field of Classification Search
CPC ... G02C 9/00; A61N 1/39; A61N 5/06; A61N 1/00; A61N 5/0616; A61M 21/00; A61B 18/18; A61F 13/02; A61H 35/02
(Continued)

(56) References Cited

U.S. PATENT DOCUMENTS

| | | |
|---|---|---|
| 1,626,617 A | 5/1927 | Last |
| 1,692,669 A | 11/1928 | Last |

(Continued)

FOREIGN PATENT DOCUMENTS

| | | |
|---|---|---|
| CN | 1738663 A | 2/2006 |
| DE | 20 20009 000 891 U1 | 7/2009 |

(Continued)

OTHER PUBLICATIONS

PCT/US2014/069789—PCT Notification Concerning Transmittal of Int'l Preliminary Report on Patentability dated Jun. 23, 2016 (Johnson & Johnson Consumer, Inc.).
(Continued)

*Primary Examiner* — William Thomson
*Assistant Examiner* — Sebastian X Lukjan
(74) *Attorney, Agent, or Firm* — Fay Sharpe LLP

(57) ABSTRACT

A radiant energy bandage system is disclosed including a plurality of therapeutic lamps and a controller for operating the lamps. Batteries power the lamps and are secured to a wearable fabric layer supporting the lamps and the controller. According to an exemplary embodiment, provided is a phototherapy device comprising a stretchable and/or flexible wearable therapeutic lamp platform including a plurality of radiant lamps configured to provide radiant energy to a user treatment area, a stretchable and/or flexible reflective wall including a plurality of radiant energy communication areas aligned with the radiant lamps and disposed to communicate the radiant energy to the user treatment area; and a stretch-
(Continued)

able and/or flexible adhesive layer including a first surface and a second surface, the first surface removably attached to the reflective layer and the second surface operatively associated with removably attaching the wearable therapeutic lamp platform to the user treatment area.

17 Claims, 42 Drawing Sheets

Related U.S. Application Data application No. 14/324,453, filed on Jul. 7, 2014, which is a division of application No. 13/604,012, filed on Sep. 5, 2012, now Pat. No. 8,771,328.

(60) Provisional application No. 61/791,738, filed on Mar. 15, 2013, provisional application No. 61/532,140, filed on Sep. 8, 2011.

(51) Int. Cl.
    *A61B 17/00* (2006.01)
    *A61B 18/00* (2006.01)

(52) U.S. Cl.
    CPC ........... *A61B 2018/00642* (2013.01); *A61B 2018/00791* (2013.01); *A61B 2018/00988* (2013.01); *A61N 2005/0626* (2013.01); *A61N 2005/0627* (2013.01); *A61N 2005/0645* (2013.01); *A61N 2005/0651* (2013.01); *A61N 2005/0652* (2013.01); *A61N 2005/0654* (2013.01); *A61N 2005/0659* (2013.01); *A61N 2005/0663* (2013.01); *A61N 2005/0665* (2013.01); *A61N 2005/0666* (2013.01)

(58) Field of Classification Search
    USPC ............... 607/88, 89; 351/47, 158; 128/898; 600/15, 27; 602/42, 43
    See application file for complete search history.

(56) References Cited

U.S. PATENT DOCUMENTS

| | | | |
|---|---|---|---|
| 3,279,468 A | 10/1966 | Le Vine | |
| 3,376,870 A | 4/1968 | Yamamoto et al. | |
| 3,971,387 A | 7/1976 | Mantell | |
| 5,085,227 A | 2/1992 | Ramon | |
| 5,616,140 A | 4/1997 | Prescott | |
| 5,824,023 A | 10/1998 | Anderson | |
| 5,913,883 A | 6/1999 | Alexander et al. | |
| 6,045,575 A | 4/2000 | Rosen et al. | |
| 6,290,713 B1* | 9/2001 | Russell | A61N 5/0616 607/88 |
| 6,293,900 B1 | 9/2001 | Bove et al. | |
| 6,350,275 B1 | 2/2002 | Vreman | |
| 6,443,978 B1 | 9/2002 | Zharov | |
| 6,471,716 B1 | 10/2002 | Pecukonis | |
| 6,508,813 B1 | 1/2003 | Altshuler | |
| 6,511,475 B1 | 1/2003 | Altshuler et al. | |
| 6,517,532 B1 | 2/2003 | Altshuler et al. | |
| 6,689,380 B1* | 2/2004 | Marchitto | A61M 37/00 424/422 |
| 6,743,249 B1* | 6/2004 | Alden | A61N 5/0601 606/1 |
| 6,824,265 B1 | 11/2004 | Harper | |
| 6,860,896 B2* | 3/2005 | Leber | A61N 5/0619 128/898 |
| 6,908,195 B2* | 6/2005 | Fuller | A61H 35/02 351/158 |
| 7,125,416 B2 | 10/2006 | Kent et al. | |
| 7,222,995 B1 | 5/2007 | Bayat et al. | |
| 7,438,409 B2 | 10/2008 | Jordan | |
| 7,520,630 B2 | 4/2009 | Murphy | |
| 7,824,241 B2 | 11/2010 | Duprey | |
| 7,896,908 B2* | 3/2011 | Ripper | A61N 5/0616 606/9 |
| 7,943,811 B2* | 5/2011 | Da Silva Macedo, Jr. | A61F 13/0203 602/42 |
| 8,192,473 B2 | 6/2012 | Tucker et al. | |
| 8,252,033 B2 | 8/2012 | Tucker et al. | |
| 8,491,118 B2 | 7/2013 | Waters | |
| 8,771,328 B2 | 7/2014 | Tapper et al. | |
| 8,858,607 B1 | 10/2014 | Jones | |
| 2003/0009205 A1* | 1/2003 | Biel | A61N 5/0601 607/88 |
| 2003/0199800 A1* | 10/2003 | Levin | A61F 13/0203 602/43 |
| 2004/0162549 A1 | 8/2004 | Altshuler | |
| 2005/0070977 A1 | 3/2005 | Molina | |
| 2005/0080465 A1 | 4/2005 | Zelickson et al. | |
| 2005/0182460 A1 | 8/2005 | Kent | |
| 2005/0278003 A1 | 12/2005 | Feldman | |
| 2006/0173514 A1 | 8/2006 | Biel et al. | |
| 2006/0217690 A1 | 9/2006 | Bastin et al. | |
| 2006/0217787 A1* | 9/2006 | Olson | A61N 5/0616 607/88 |
| 2006/0268220 A1 | 11/2006 | Hogan | |
| 2007/0156208 A1 | 7/2007 | Havell et al. | |
| 2007/0208395 A1 | 9/2007 | Leclerc et al. | |
| 2007/0233208 A1 | 10/2007 | Kurtz et al. | |
| 2007/0239232 A1* | 10/2007 | Kurtz | A61N 5/0613 607/87 |
| 2008/0058915 A1* | 3/2008 | Chang | A61H 39/002 607/140 |
| 2008/0065056 A1 | 3/2008 | Powell et al. | |
| 2008/0269849 A1 | 10/2008 | Lewis | |
| 2009/0143842 A1 | 6/2009 | Cumbie et al. | |
| 2009/0192437 A1 | 7/2009 | Soltz et al. | |
| 2010/0023927 A1* | 1/2010 | Yang | G06F 21/10 717/120 |
| 2010/0069898 A1 | 3/2010 | O'Neil et al. | |
| 2010/0121254 A1* | 5/2010 | McDaniel | A61B 18/203 604/20 |
| 2010/0121419 A1 | 5/2010 | Douglas | |
| 2011/0015707 A1 | 1/2011 | Tucker et al. | |
| 2011/0040355 A1 | 2/2011 | Francis | |
| 2011/0160814 A2 | 6/2011 | Tucker et al. | |
| 2011/0257467 A1 | 10/2011 | Clegg et al. | |
| 2012/0116485 A1 | 5/2012 | Burgmann | |
| 2012/0323064 A1 | 12/2012 | Kim | |

FOREIGN PATENT DOCUMENTS

| | | |
|---|---|---|
| EP | 1 074 275 A1 | 2/2001 |
| EP | 1 916 016 A1 | 4/2008 |
| GB | 2 380 134 A | 4/2003 |
| WO | WO2004052238 | 12/2003 |
| WO | WO 2006/028461 A2 | 3/2006 |
| WO | WO 2010/076707 A1 | 7/2010 |
| WO | WO2011049419 | 10/2010 |

OTHER PUBLICATIONS

PCT/US2016/038606—PCT Notification Concerning Transmittal of Int'l Preliminary Report on Patentability dated Nov. 15, 2016 (Johnson & Johnson Consumer, Inc.).
PCT/US2016/038607—PCT Notification Concerning Transmittal of Int'l Preliminary Report on Patentability dated Sep. 29, 2016 (Johnson & Johnson Consumer, Inc.).
PCT/US2016/038608—PCT Notification Concerning Transmittal of Int'l Preliminary Report on Patentability dated Sep. 29, 2016 (Johnson & Johnson Consumer, Inc.).
PCT/US2016/038612—PCT Notification Concerning Transmittal of Int'l Preliminary Report on Patentability dated Sep. 29, 2016 (Johnson & Johnson Consumer, Inc.).

(56) References Cited

OTHER PUBLICATIONS

PCT/US2014035009; Extended European Search Report; 8 pages, J&J Consumer Inc., Munich, Dec. 14, 2016.

* cited by examiner

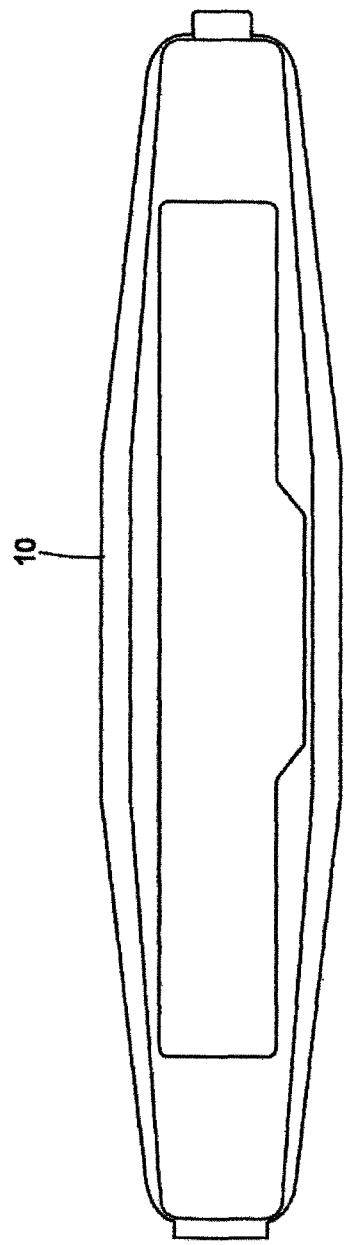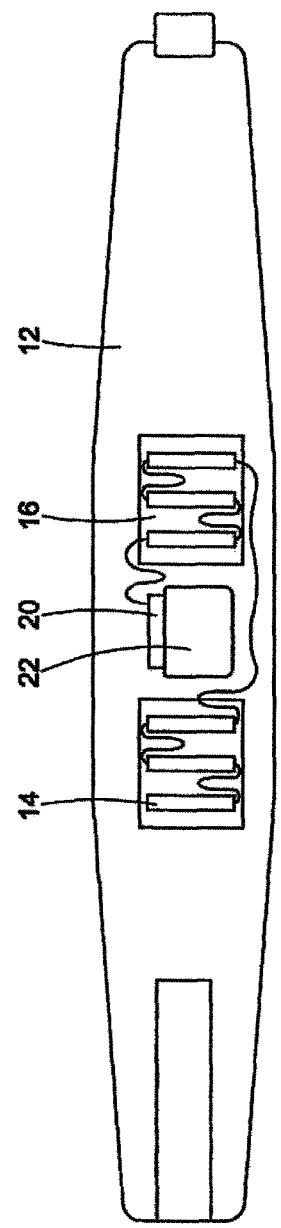
FIG. 1A
FIG. 1B

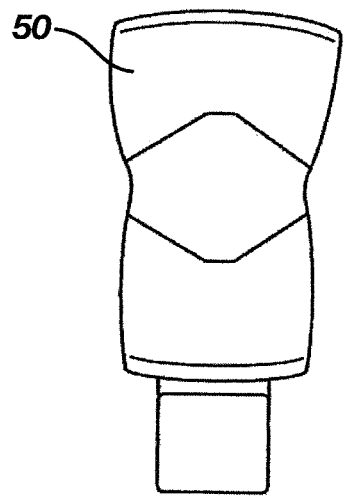 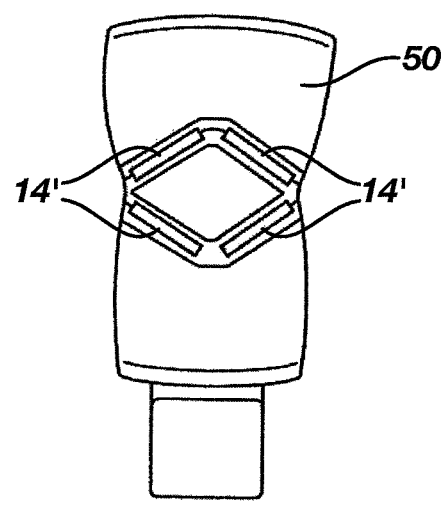
FIG. 4A   FIG. 4B
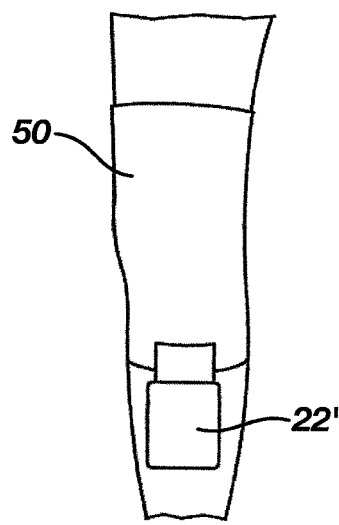 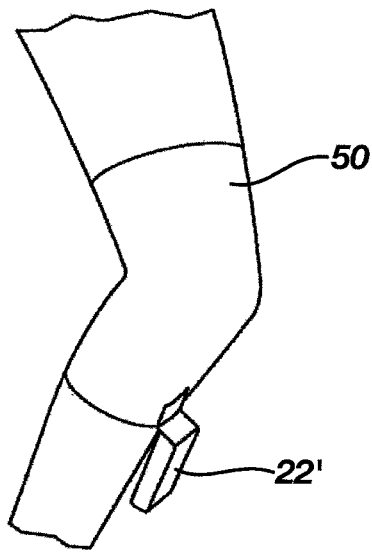
FIG. 4C   FIG. 4D

LIGHT THERAPY BANDAGE SYSTEM

This application is a continuation-in-part of U.S. patent application Ser. No. 14/212,601, filed Mar. 14, 2014, which claims priority to U.S. Provisional Patent Application Ser. No. 61/791,738, filed Mar. 15, 2013, and this application is a continuation-in-part of U.S. patent application Ser. No. 14/324,453, filed Jul. 7, 2014, which is a divisional of U.S. patent application Ser. No. 13/604,012, filed Sep. 5, 2012 now U.S. Pat. No. 8,771,328, which claims priority to U.S. Provisional Patent Application Ser. No. 61/532,140, filed Sep. 8, 2011, the disclosures of which are incorporated herein by reference.

INCORPORATION BY REFERENCE

"Light Therapy Platform System", U.S. Patent Publication No. US 2013-0066404 A1, published on Mar. 14, 2013, by Tapper et al., the disclosure of which is incorporated herein by reference in its entirety.

FIELD

The present embodiments relate to devices and methods for delivering light-based skin therapy treatments for improving skin health, and/or relieving subdermal tissue using light-emitting diode (LED) light therapy, although other types of light radiating sources can be used.

BACKGROUND

Certain light spectrums emitted by LEDs (blue or red) are known to be therapeutic for skin treatment by being beneficial to better factor wound healing or relieving muscular or other subdermal tissue pain. However, there is a need to provide users/patients with a convenient at-home light therapy delivery device such as a wearable bandage that is adjustable or flexible to conform to different sizes and shapes, and that is simple to use without user discomfort. The alternative is visiting a doctor's office to receive treatments.

Prior known light therapy devices have suffered from problems relating to the exposure of the LEDs and the associated circuitry to power the LEDs to contact by users. More particularly, in an effort to maximize light communication to a patient, the LEDs have been disposed in a manner which allow them to be physically engaged (e.g., touched) by a patient, or even contact a treatment surface, which processes are debilitating to the LEDs as a result of the accumulation of dirt and oil. In addition, any such engagement can be potentially dangerous to patients who are exposed to the sharp or hot edges of the LEDs and the associated circuitry. The exposure of detailed circuitry presents an intimidating and unpleasant experience.

Another problem with prior known devices is that the LED arrangement is fixed and not adjustable to better correspond to wound location, size or shape, or to be better placed relative to pain areas. The LEDs of such devices are not selectively arrangeable in a variety of patterns to better enable the application of the device near particular pain areas of a wound.

It is desired to provide alternative means of using the benefits of the light therapy in a manner to maximize therapeutic efficiencies in exposure while maintaining ease and convenience of use. For this reason, a variety of light weight, flexible and adjustable embodiments are disclosed within this disclosure incorporating a variety of energy varying applications responsive to user conditions or needs.

SUMMARY

According to an exemplary embodiment of this disclosure, provided, a phototherapy system and device includes a therapeutic lamp platform for radiant lamps such as LEDs which are disposed in an assembly comprising a multi-layer structure wherein the LEDs are guarded from patient contact.

The exemplary embodiments disclosed provide an adjustable/flexible platform for providing a light-based therapy that is adaptable to the user's receptive surfaces, i.e., treatment areas, whether based on size or condition, wherein the light therapy can be applied without limitation of the kind of light and without limitation of the ultimate purpose of the therapy, i.e., beauty, health, pain relief and/or wound healing. Such sources can vary in the form of the radiant energy delivery. Pulsed light (IPL), focused light (lasers) and other methods of manipulating light energy are encompassed within the presently disclosed embodiments. Other methods of light emission may include continuous, pulsed, focused, diffuse, multi wavelength, single wavelength, visible and/or non-visible light wavelengths.

According to an exemplary embodiment of this disclosure, forms such as a shaped/fitted bandage with LED light emitted from LED bulbs or LED strips that are capable of being adjusted to accommodate variances in a desired treatment area.

According to one exemplary embodiment of this disclosure, a phototherapy device is provided which includes a stretchable and/or flexible wearable therapeutic lamp platform including a plurality of radiant lamps configured to provide radiant energy to a user treatment area; a stretchable and/or flexible reflective wall including a plurality of radiant energy communication areas aligned with the radiant lamps and disposed to communicate the radiant energy to the user treatment area; and a stretchable and/or flexible adhesive layer including a first surface and a second surface, the first surface removably attached to the reflective layer and the second surface operatively associated with removably attaching the wearable therapeutic lamp platform to the user treatment area.

According to another exemplary embodiment of this disclosure, provided is a stretchable and/or flexible wearable phototherapy device including a plurality of radiant energy pods, each pod including one or more radiant lamps to provide radiant energy to a user treatment area, and each pod stretchably and flexible connected to one or more other pods; and a control pod stretchably and flexibly connected to one or more radiant energy section, the control pod operatively connected to the radiant energy pods and configured to control an operation of the radiant lamps.

The present disclosure thus describes a fully stretchable and/or flexible and adjustable LED device which provides improved usability and light dispersion. Such a device includes a light therapy bandage system including a spacing and/or insulating layer to effectively elevate the lamp radiation from the patient's treatment area (e.g. skin). According to one exemplary embodiment, the lamps are recessed relative to the insulating layer and further covered by a sheer mesh layer to protect the user from being able to contact the lamps. Moreover, the disclosed embodiments may or may not be used with lotions, creams and/or ointments which enhance the efficacy of the delivered phototherapy radiation to provide treatment to a user treatment area.

BRIEF DESCRIPTION OF THE DRAWINGS

FIG. 1A is a plan view of an exemplary embodiment of a therapeutic lamp platform including a lumbar brace according to this disclosure;

FIG. 1B is an opposite plan view of the therapeutic lamp platform of FIG. 1A;

FIG. 4A is a perspective view of another exemplary embodiment of a wearable therapeutic lamp platform including a knee brace according to this disclosure;

FIG. 4B is an alternative view of the device of FIG. 4A;
FIG. 4C is an alternative view of the device of FIG. 4A;
FIG. 4D is an alternative view of the device of FIG. 4A.

DETAILED DESCRIPTION

The subject embodiments relate to a phototherapy system including methods and devices, preferably comprising a wearable device integrated with a portable battery pack for powering therapeutic lamps in the device. The subject devices display numerous benefits including a light platform wherein the platform and the lamps therein are properly positionable relative to a user treatment area during use, where no human touch is required during treatment. That is, structural componentry of the device not only supports the lamp platform on the user, but functions as a guide for the appropriate disposition of the lamps relative to the treatment areas of the user. The structural assembly of the device precludes sharp or hot surfaces from being engageable by a user as the lamps are recessed relative to an inner reflective surface nearer to and facing the patient treatment surface. Circuit componentry to communicate power to the lamps is also encased within a flexible and stretchable wall structure. Therapeutic light, shining through wall radiant energy communication areas, such as, but not limited to, apertures, mesh and clear/translucent layers, is communicated to the user while the lamps and the circuitry are effectively covered within the layered wall structure. A surface is thus presented to the user that is properly spaced for the desired therapeutic treatments, yet provides improved ventilation so that an aesthetic and appealing device surface is presented to the user that minimizes user discomfort. Other benefits relate to the adjustability of the device in the form of a bandage which forms upon user receipt to match a treatment surface, e.g., back or knee, of the user. The overall assembly is purposefully constructed of relatively light weight and minimized componentry for ease of user use and comfort.

Figure 2:
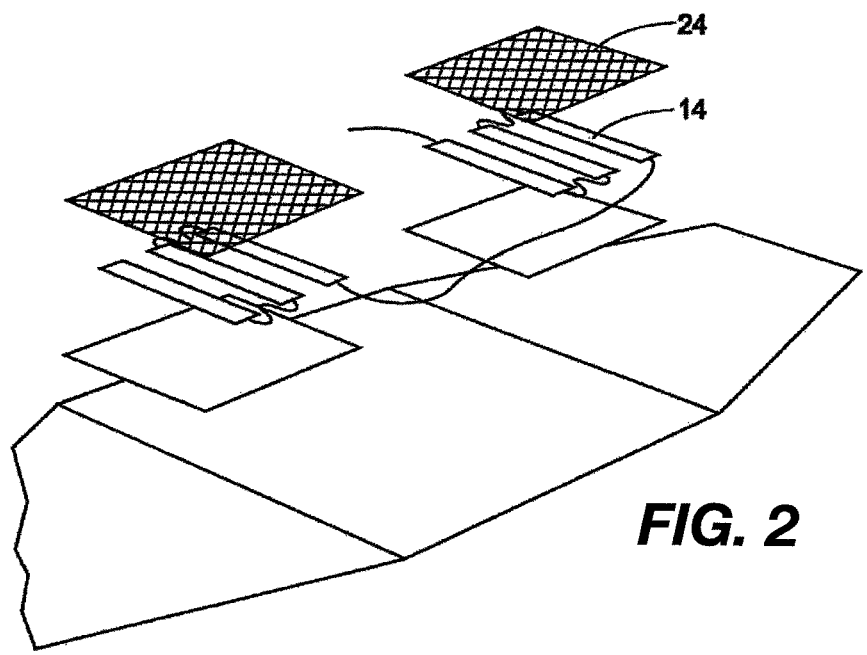
FIG. 2 is an exploded view of the therapeutic lamp platform shown in FIGS. 1A and 1B.
Figure 3:
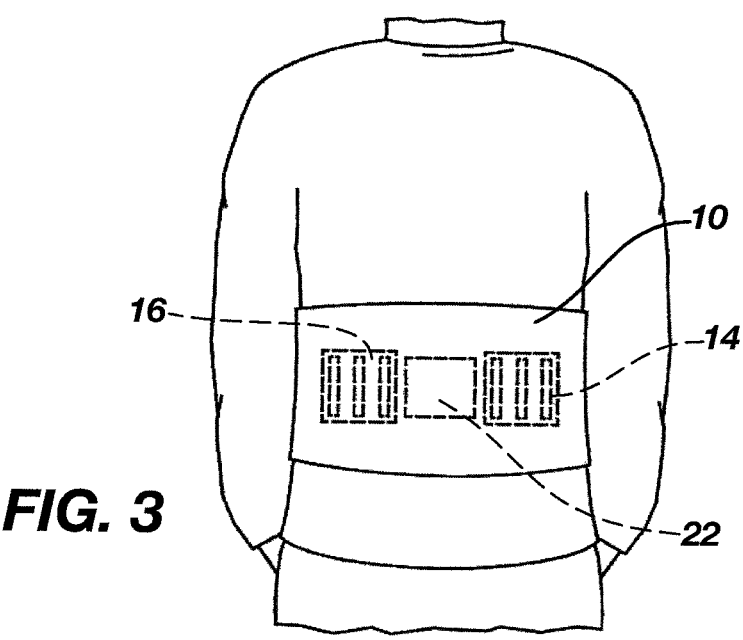
FIG. 3 is a perspective view of the device shown in FIGS. 1A and 1B on a patient.

More particularly, and with reference to FIGS. 1A, 1B and 2, an exemplary embodiment is shown including a lumbar brace 10 that can be worn by a patient/user such as shown in FIG. 3. The brace 10 can be supported and affixed on the user by a hook-and-loop locking fabric at the terminal ends of the brace. Such a brace can include heat wraps for lower back and hips 14 on the exterior of the brace 10 opposite of the patient facing surface. The LED platform of the bandage includes an elastic member 12 on which LED strips 14 are mounted on a support layer 16 that is heat insular and/or reflective. It is important that the layer 16 be flexible and stretchable with the elastic bandage 12. Note that the wires connecting the LEDs to the battery pouch 22 are of extra length to allow stretching of the dimension between the LED strips. Power is supplied by a battery pack 20 received in battery pouch 22. The LED lights 14 are spaced from direct engagement of the patient by an insular layer 24 which can range from a mesh cloth to a flexible sheet of formable material in which the strips are integrally molded.

In one exemplary embodiment, the mesh cloth allows communication of the lamp radiation through to the patient without reflection.

In another exemplary embodiment, the flexible formable material 24 has apertures (not shown) functioning as a window to allow the light to pass through and the remainder of the material 24 includes a light reflective surface. In this embodiment, the LEDs are effectively hidden from the patient, where layer 24 is a mesh cloth where the patient can see the LEDs tips and the associated circuitry.

The subject system may also include control systems to vary light intensity, frequency or direction. A portable battery pack is integrated to the wearable phototherapy device, and may include a removable replaceable battery pack or a rechargeable battery pack.

The subject adjustability can be implemented through "smart" processing and sensor systems for enhanced flexibility/adjustability in the form of adjustable energy output, adjustable wavelengths, priority zones, timers, and the like. The sensors of the sensor systems enable the subject embodiments to have the ability to evaluate the treatment area and plan a smart treatment, utilizing more or less energy on the priority zones. The subject embodiments can also be smart from the standpoint of body treatment area such as knee or back, and of skin type, age, overall severity of problems and have the ability to customize the treatment accordingly.

In yet another exemplary embodiment, the lamps are embedded in a flexible sheet of formable material and are integrally molded as strips within a material sheet.

Figure 5:
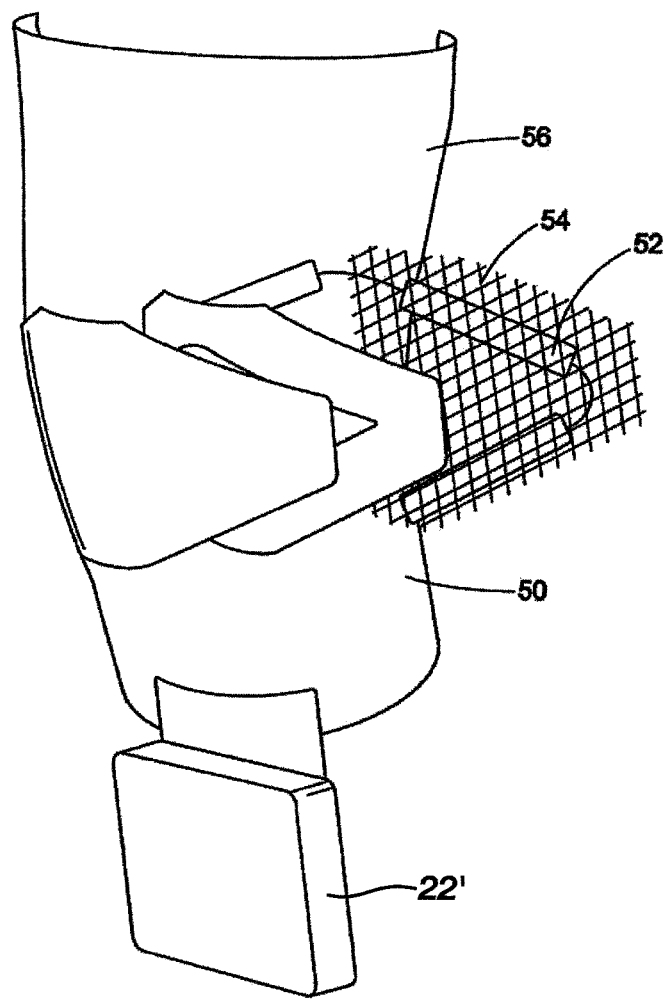
FIG. 5 is an exploded perspective view of the device of FIG. 4A.

With reference to FIGS. 4A, 4B, 4C, 4D and 5, an exemplary LED bandage is shown where LED strips are arranged in a diamond pattern and the elastic bandage is formed as a unitary sleeve which is pulled over the leg to the knee area. The multi-structural layer of the brace is shown in FIG. 5 and includes an elastic bandage platform 50, a first layer reference material that may be constructed of emergency blanket material 52, LED light strips 54, and a surface layer 56 to cover the strips 54.

Figure 6:
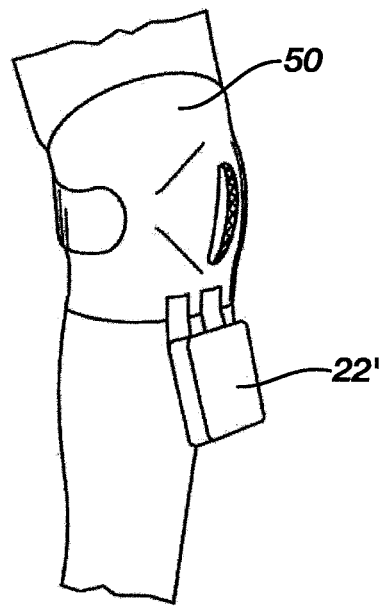
FIG. 6 is an alternative exemplary embodiment of a knee brace according to this disclosure.
Figure 7:
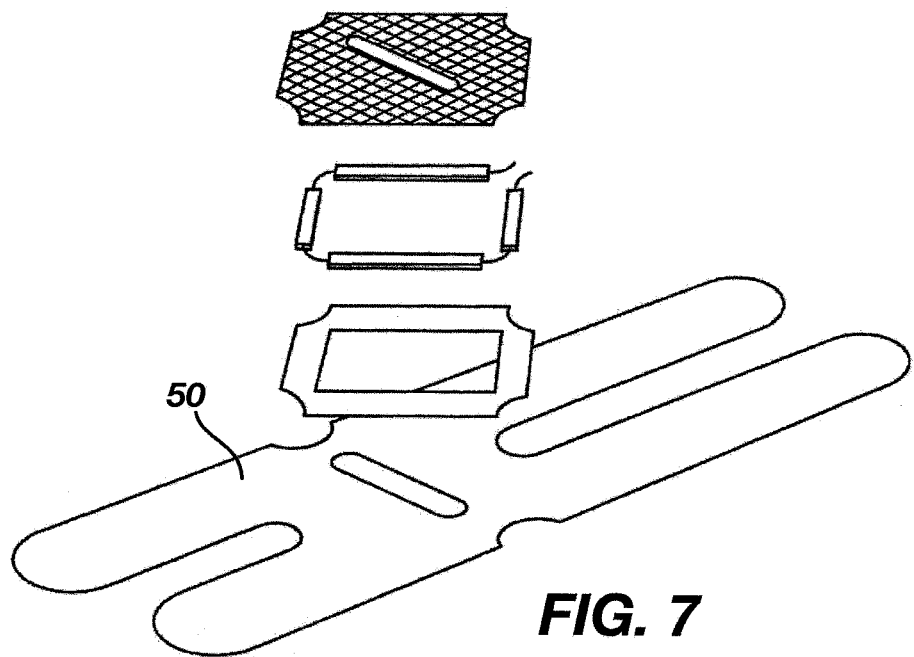
FIG. 7 is an exploded view of the device of FIG. 6.

With reference to FIGS. 6 and 7, another alternative embodiment of a knee brace is shown where an elastic bandage is wrapped around a knee as shown in FIG. 6, again the elastic bandage includes a diamond pattern about the patient's kneecap including the multi-layer structures such as is shown in FIG. 7.

Figure 8:
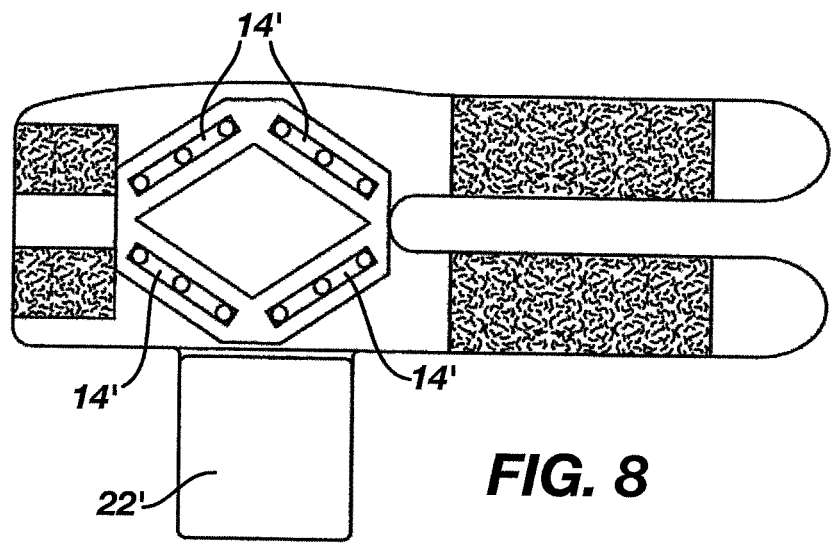
FIG. 8 is another embodiment of a knee brace.
Figure 9:
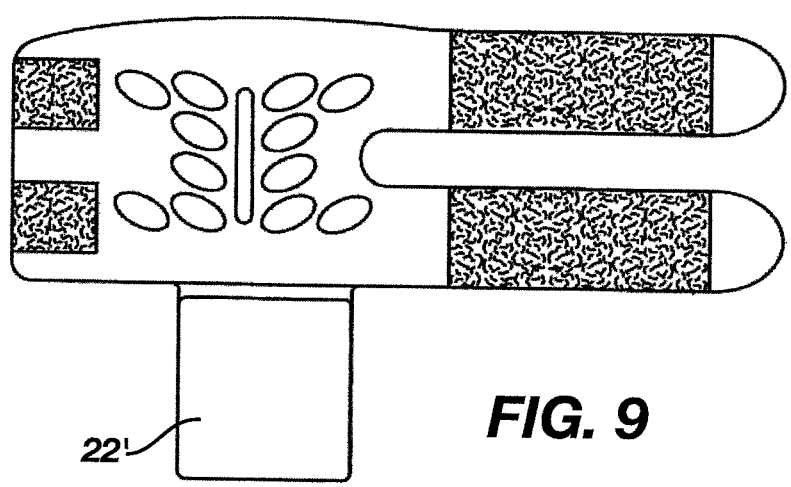
FIG. 9 is another embodiment of a knee brace.

FIGS. 8 and 9 show yet other embodiments which can also function as a wraparound knee brace including the same multi-layer structures such as is shown in FIG. 9.

In other embodiments, the LED strip pattern can be arranged in different placements as shown in the figures to better match treatment to the desired patient treatment area. For example, rather than being equally spaced, the strips can be bunched together in a group, or several groups, where the bandage material is constructed of a material that allows the LED strips to be selectively moved and then affixed to the material at different locations, for example, hook-and-loop fastening fabric.

Figure 10:
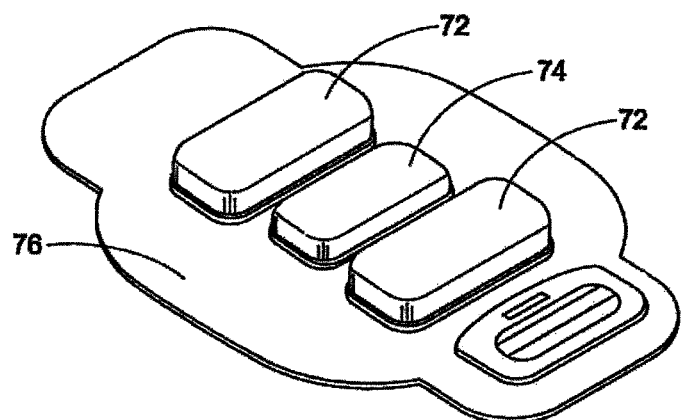
FIG. 10 is a top perspective view of one embodiment of the subject bandage system.
Figure 11:
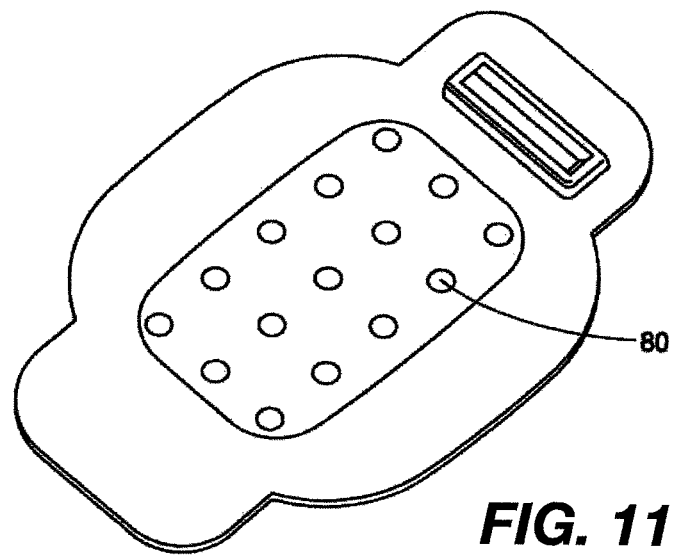
FIG. 11 is a bottom view of the device of FIG. 10.

FIGS. 10 and 11 show another embodiment wherein battery energy sources 70 are encased in battery shrouds 72 and operatively connected to a controller 74 attached to a primary fabric layer 76. FIG. 10 shows the top layer of the device away from a user treatment area (not shown). FIG. 11 shows the bottom surface of the device of FIG. 10 wherein the therapeutical lamps of radiation communicate to the treatment area through a plurality of spacer window openings 80.

Figure 12:
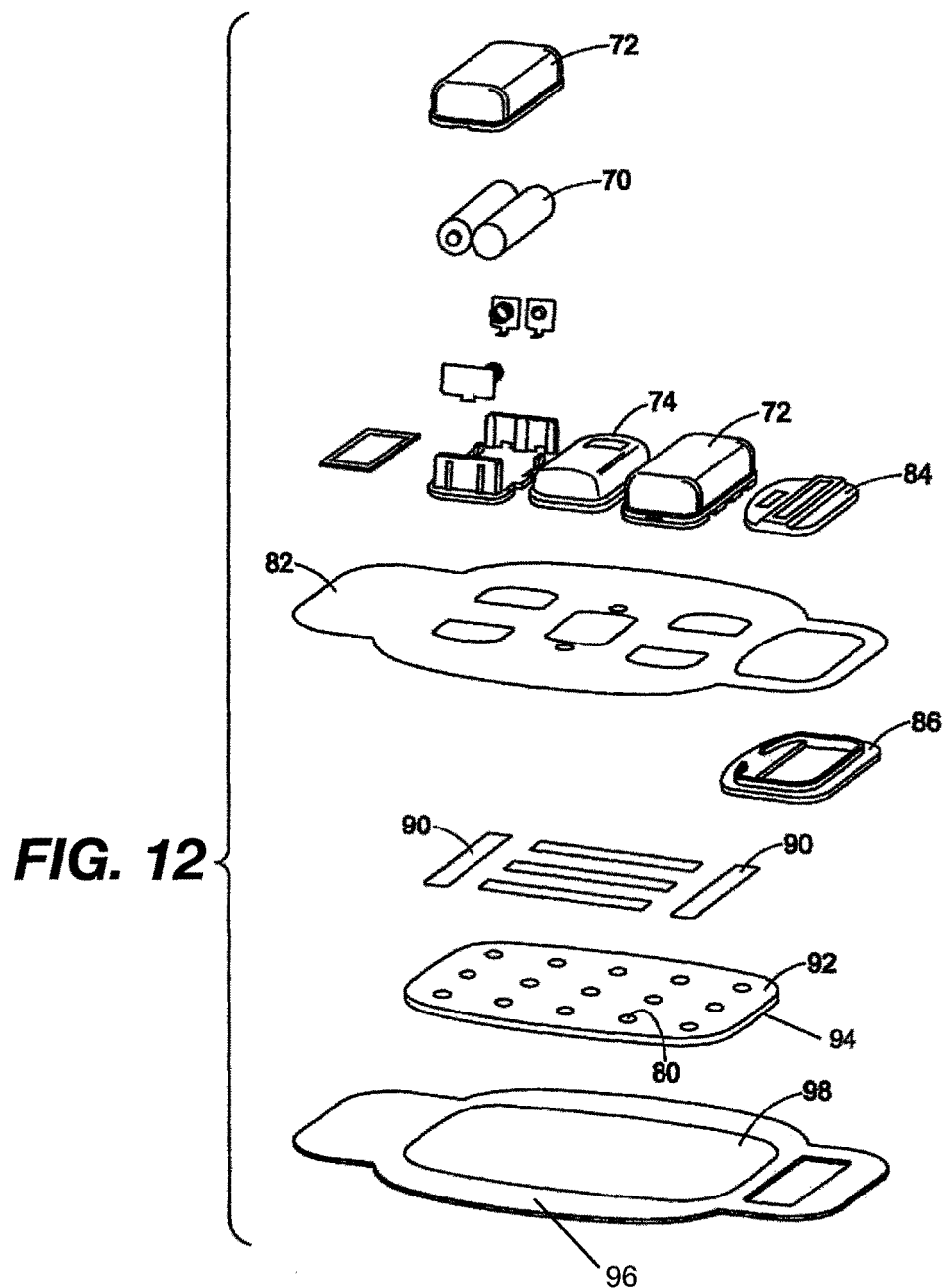
FIG. 12 is an exploded view of the device of FIG. 10.

FIG. 12 shows more clearly the component elements of the device. The battery pack 72 and controller 74 are either mechanically attached or heat bonded to the primary fabric layer 82 which can be secured to a patient treatment area through a strap (not shown) received in a buckle 84 and buckle receiver 86 assembly. According to an exemplary embodiment, the therapeutic lamps include a plurality of LED strips 90 mounted on a foam 92 and reflective layer 94 in a manner so that the LEDs are aligned with the windows 80. Power to the LED strips 90 is communicated from the battery 72 via wires (not shown). The foam 92 and reflective layer 94 includes a heat insulator and spacer so that the LEDs mounted on the strips 90 are recessed relative to the opposite surface of the foam layer 92, rather than the surface on which they are mounted. The strips 90 and foam layer 92 form a subassembly that in one embodiment is selectively removable and replaceable from and to the device. Layer 92 is highly flexible as are the strips 90 so that the strip 90 and layer 92 subassembly is flexible along a plurality of directions aligned with the areas intermediate the strips for the overall purpose of providing a device which is conformable to properly and comfortably cover a non-flat treatment area. The layer 92 is dimensioned so that the lamps on the LED strips 90 don't break the surface plane of layer 92 on which a reflective layer 94 is attached. According to an exemplary embodiment, reflective layer 94 includes a flexible foil suitable for reflecting the radiant energy of the lamps. A secondary fabric layer covers the foam 92 and reflective layer 94 with a sheer mesh 98 which allows lamp radiation to be communicated to the treatment area with minimal obstruction. The effect is that of a plurality of expanding cones of radiant energy from the lamps of the LED strips 90 that is communicated through the foam layer 92 and reflective layer 94 for therapeutic treatment of the treatment area.

The controller 74 is configured to communicate operational aspects of the device to the user in several ways. When the user actuates an ON switch, an indicator such as a light or beep sounder lets the user know that the device is operating. The controller times the operation to a predetermined limit such as 10 or 15 minutes. In addition, the controller counts usage or cycle sessions to indicate to the user via a controller display, the number of sessions that have been provided by the device and additionally, to disable the device after the LED efficiency in generating therapeutic radiation has been diminished from prior sessions such that the device should no longer be used. The controller also deactivates the indicator light after the session duration has been timed out or may alternatively send another sound beep to the user. Alternatively, the indicator can also provide for indicating battery life or lamp failure.

With reference to FIGS. 13-22, illustrated is a stretchable, flexible, and wearable therapeutic lamp platform according to another exemplary embodiment of this disclosure, also referred to as a phototherapy device throughout this disclosure.

Figure 13A:
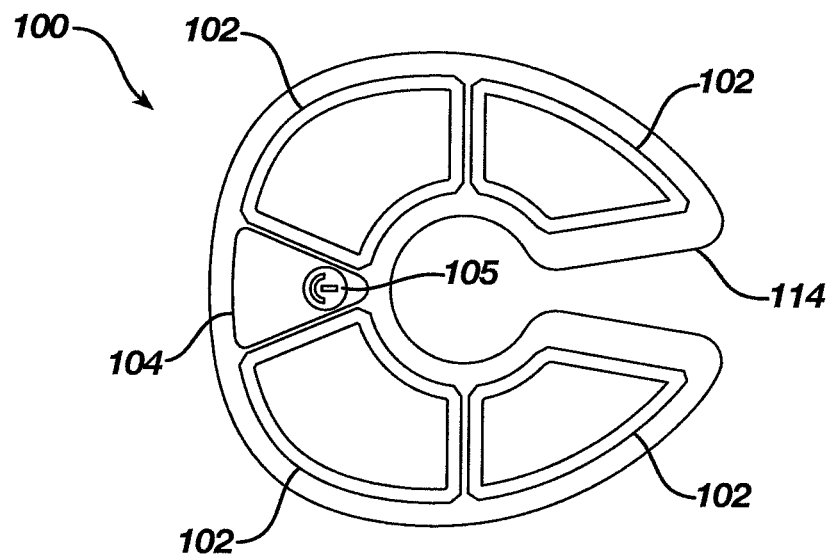
FIGS. 13A and 13B illustrate a stretchable and bendable wearable therapeutic lamp platform according to an exemplary embodiment of this disclosure.
Figure 13B:
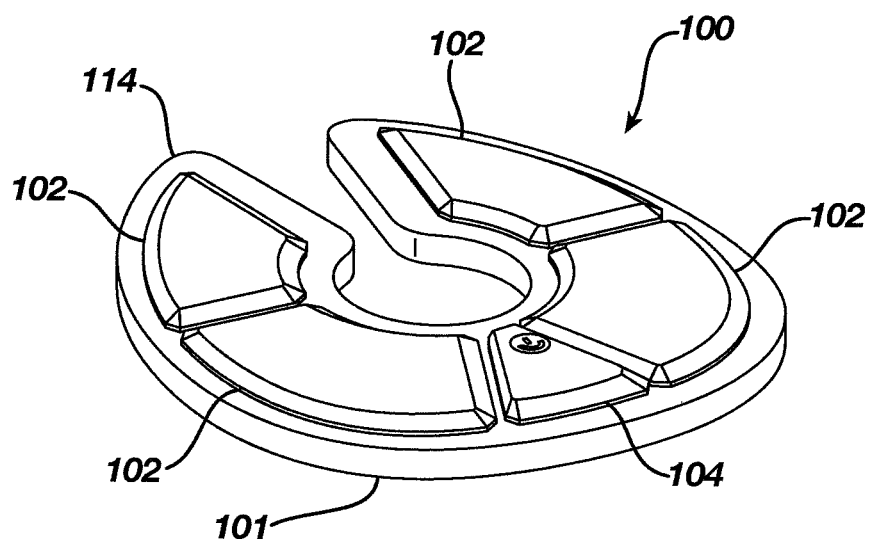

FIG. 13A is a top view of the phototherapy device and FIG. 13B is a perspective view of the phototherapy device, as seen by a user. As shown, the phototherapy device is substantially U-shaped or horseshoe shaped, which provides a significant degree of conformability of the device to a plurality of user treatment areas, including but not limited to, ankles, elbows, knees, shoulders, and other body joints, as well as feet. While the application of the phototherapy therapy device shown in FIGS. 13-22 is not limited to any specific user treatment areas, it is especially suited for joints where the device goes around bony joints and treats the muscles/tendons/tissues around the joint.

While the exemplary embodiment described with reference to FIGS. 13-22 includes a U-shaped phototherapy device, it is to be understood other shapes are within the scope of the disclosure, for example, but not limited to, circular shaped, square shaped, rectangular shaped, oval shaped, etc.

As shown in FIGS. 13A and 13B, the exemplary phototherapy device 100 includes a plurality of pods 102 which house one or more batteries and a pod 104 which houses a controller and ON/OFF button switch 105. During operation, the phototherapy device emits therapeutic radiation 101 to a user treatment area to relieve pain and/or provide therapeutic treatment for healing of the user treatment area.

Figure 14:
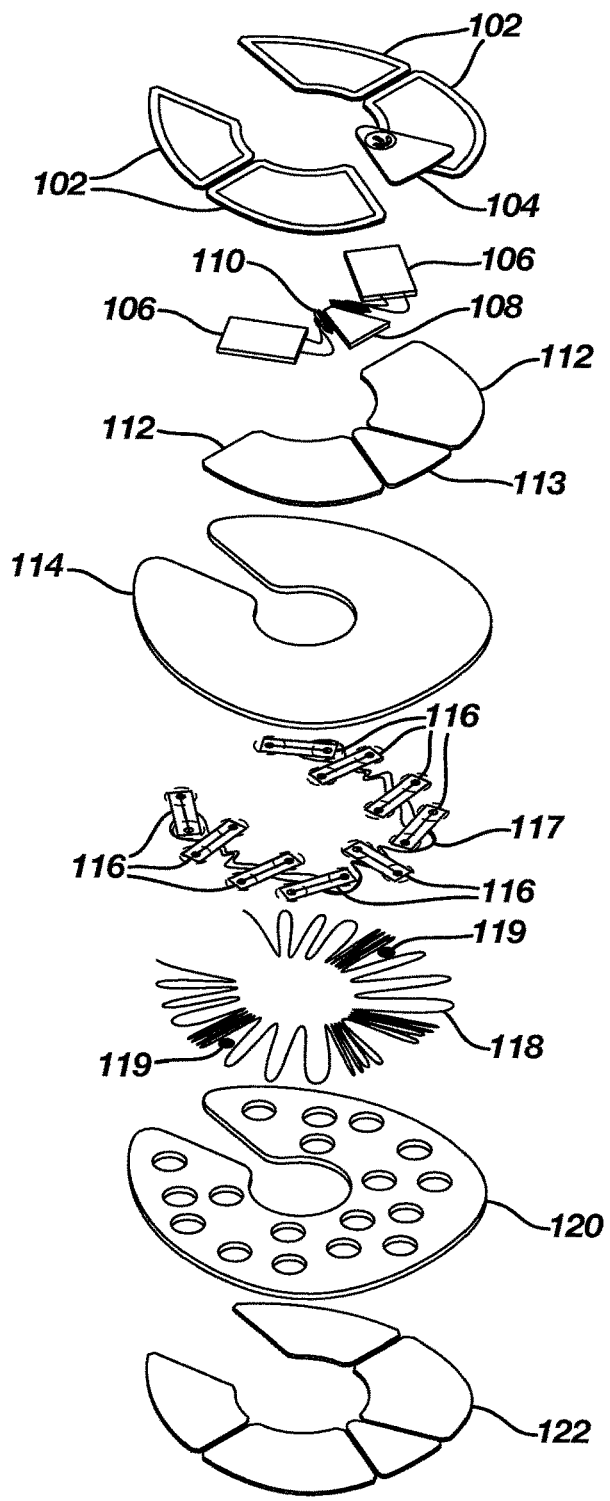
FIG. 14 is an exploded view of the stretchable and bendable wearable therapeutic lamp platform illustrated in FIGS. 13A and 13B.

With reference to FIG. 14, illustrated is an exploded view of the stretchable, flexible, and wearable therapeutic lamp platform shown in FIGS. 13A and 13B. The phototherapy device includes hard surface pods 102, a controller pod 104, batteries 106, a controller 108, wires 110 which operatively connect the controller 108 to the batteries 106, pod bottoms 112, controller pod bottom 113, a stretchable and flexible top layer 114, LED strips 116 operatively connected with flexible LED connection wires 117, heating component 118 including temperature sensors 119, a stretchable and flexible bottom layer 120, a reflective layer 122 (note: LED clearance holes not shown) and a biomedical sticky gel.

As shown, the heating element 118 is arranged in a pattern which covers the general shape of the phototherapy device and provides heat to a user treatment area. Essentially a wire, such as a Nichrome® wire driven by the controller 108 provides heat and temperature sensors 119 provide feedback to the controller 108 to regulate the radiated heat provided to the user treatment area, in addition to ramping up the initial heat provided after the phototherapy device is turned ON, for example ramping quickly to maintain a temperature between 40-45 Celsius.

The structure of the phototherapy device provides a stretchable, flexible and conformable, therapeutic lamp platform which can be applied to a variety of user treatment areas. In other words, the phototherapy device is conformable to user treatment area in three dimensions.

Figure 15:
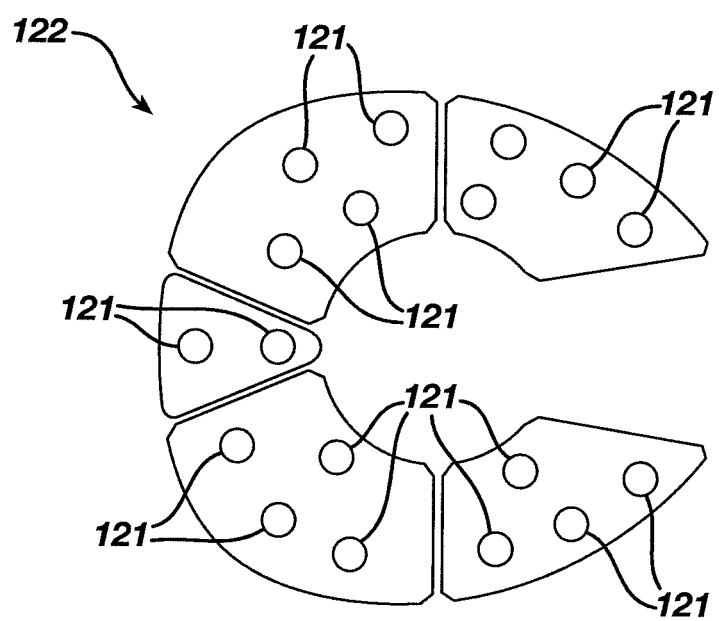
FIG. 15 is a plan view of the reflective layer as shown in FIG. 14.

With reference to FIG. 15, illustrated is a plan view of the reflective layer 122 as shown in FIG. 14, except LED clearance holes 121 are shown.

The reflective layer includes a plurality of lamp radiation communication areas 121, such as apertures, clearance holes and/or areas of the reflective layer 122 aligned with the LEDs which are transmissive to the wavelength of the radiation emitted from the LEDs. In other words, the lamp radiation communication areas can be made of a clear or translucent flexible material, where a reflective layer or film, such as a reflective metal foil or PET reflective material is applied to the bottom, i.e. reflective surface of the reflective layer 122, using a masking process to maintain the radiation transmissive characteristics of the radiation communication areas 121. In addition to reflecting lamp radiation, the reflective layer 122 material can include insulating material to contain heat within the user treatment area for effectively treating pain, etc.

As an alternative arrangement, the phototherapy device can integrate the reflective layer 122 with a biomedical sticky gel as a single usable substrate. In other words, the sticky gel, which is replaceable by a user, would include a replaceable reflective layer incorporated into the sticky gel, where a reflective material is encased within the sticky gel.

Sticky gel is a "sticky" adhesive gel compound which removably adheres to the phototherapy device structure reflective layer 122 and a user treatment area. The sticky gel layer is made of a material which also is substantially transparent to the LED lamp radiant emitted by the phototherapy device or includes apertures to communicate the LED lamp radiation. Examples of a suitable material include silicon, hydrogel acrylic and urethane based material.

According to an exemplary embodiment, the sticky gel component includes multiple layers integrated into a single replaceable structure, where a top layer material has properties to provide a bond to the phototherapy device structure and a bottom layer material has properties to provide desirable adhesive properties to a user treatment area. In addition, a third layer material between the top and bottom layers can be provided to act as a structural component to maintain the form of the sticky gel component.

Figure 16:
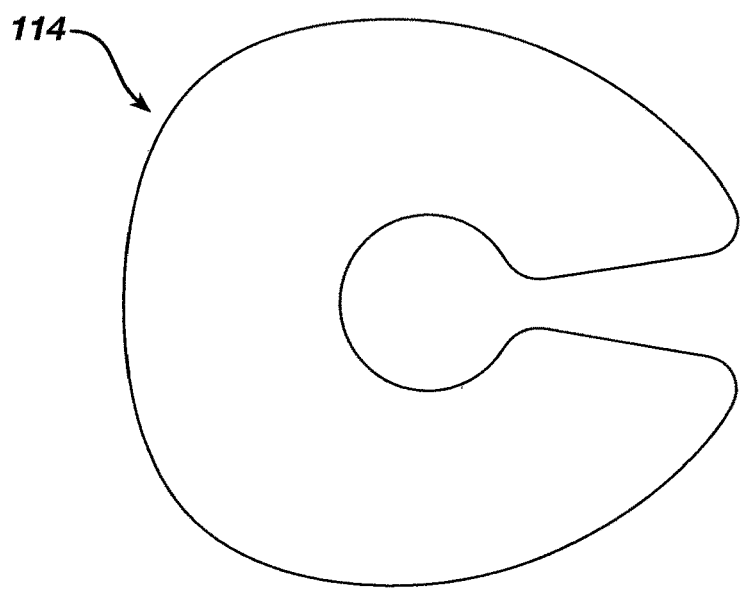
FIG. 16 is a plan view of the stretchable and bendable top layer as shown in FIG. 14.
Figure 17:
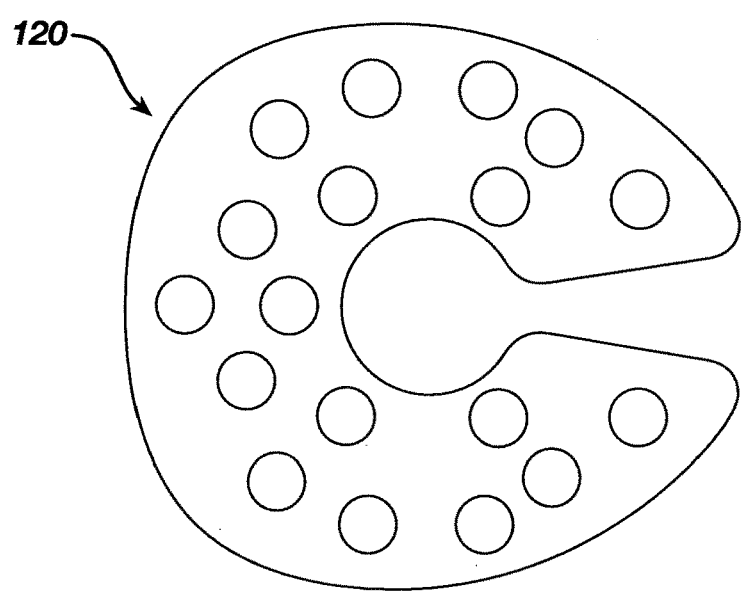
FIG. 17 is a plan view of the stretchable and bendable bottom layer as shown in FIG. 14.

With reference to FIG. 16, illustrated is a plan view of the flexible and stretchable top layer as shown in FIG. 14 and FIG. 17 is a plan view of the flexible and stretchable bottom layer 120 as shown in FIG. 14.

The flexible and stretchable top layer 114 and bottom layer 120 provide a flexible and stretchable housing for LED strips 116, wires 117, an optional heating element 118 and optional temperatures sensors 119. The stretchable layers 114 and 120 can be made from, for example, a low durometer silicone TPE, and/or fabric. As shown in FIG. 17, the flexible bottom layer 120 includes a plurality of LED radiation communication areas, i.e. apertures, to provide radiation to a user treatment area.

Figure 18:
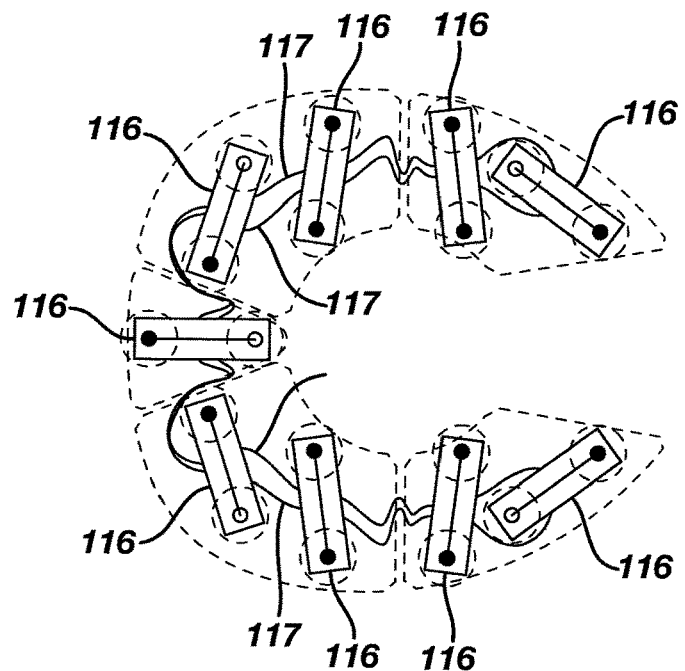
FIG. 18 shows a layout of LED strips according to an exemplary embodiment of this disclosure as shown in FIG. 14.

With reference to FIG. 18, shown is a layout of LED strips 116 according to an exemplary embodiment of this disclosure as shown in FIG. 14.

The LED strips 116 include a plurality of LEDs which are operatively connected by wires 117. According to an exemplary embodiment, 18 LEDs of two different wavelengths are provided, where 6 LEDs provide IR (Infrared Spectrum Radiation) for inflammation relief and 12 LEDs provide R (Red Spectrum Radiation).

Figure 19:
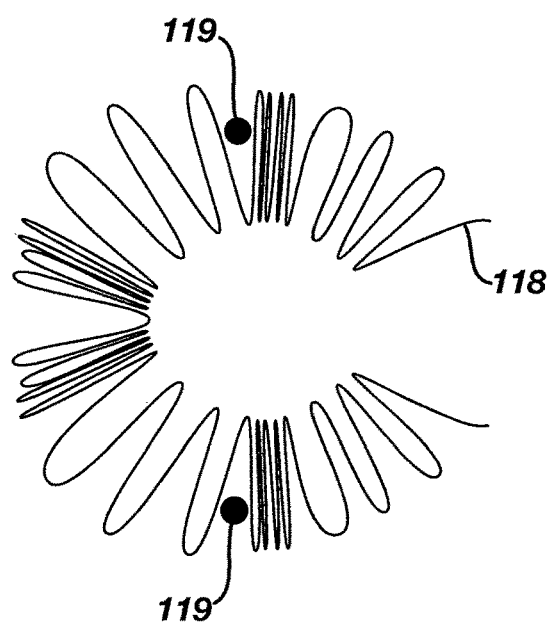
FIG. 19 is an enlarged detail view of the heating component and temperature sensor(s) arrangement as shown in FIG. 14.

With reference to FIG. 19, illustrated is an enlarged detail view of the optional heating component 118 and temperature sensor(s) 119 arrangement as shown in FIG. 14.

Figure 20:
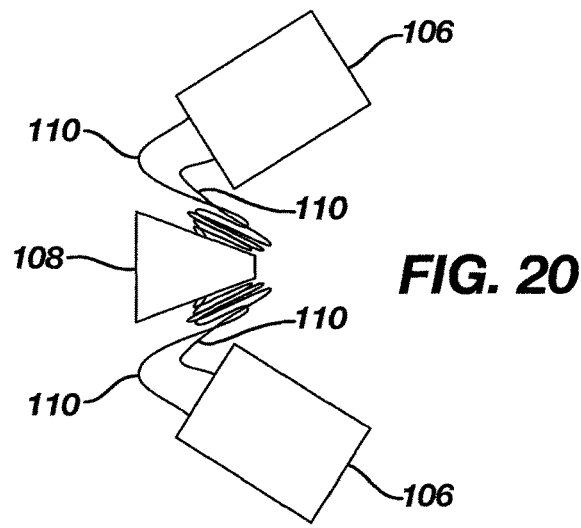
FIG. 20 is an enlarged detail view of the circuit board, i.e., controller, and the battery arrangement as shown in FIG. 14.

With reference to FIG. 20, illustrated is an enlarged detail view of the circuit board, i.e., controller, and the battery arrangement as shown in FIG. 14.

As shown, included are two batteries 106, a controller 108 and wires 110 which operatively connect batteries 106 to the controller 108. A suitable length of wires 110 provides a stretchable and flexible configuration where the wires 110 are free to expand and contract while maintaining electrical conductivity between the controller 108 and batteries 110, as well as between the controller 108 and LED strips 116.

Figure 21:
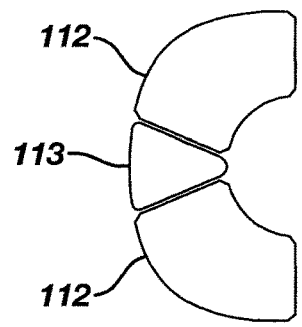
FIG. 21 is an enlarged detail view of the bottom casing for housing the circuit board and batteries as shown in FIG. 14.

With reference to FIG. 21, illustrated is an enlarged detail view of the bottom casing for housing the circuit board and batteries as shown in FIG. 14.

Figure 22:
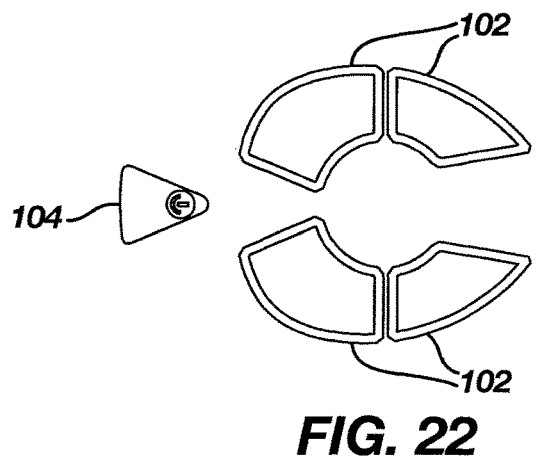
FIG. 22 is an enlarged detail view of the top casing for housing the circuit board and batteries as shown in FIG. 14.

With reference to FIG. 22, illustrated is an enlarged detail view of the top casing for housing the circuit board and batteries as shown in FIG. 14.

With reference to FIGS. 23-31, illustrated is a flexible wearable therapeutic lamp platform according to another exemplary embodiment of this disclosure, also referred to as a phototherapy device throughout this disclosure. The size and construction of this light therapy platform is especially suited to provide phototherapy to user treatment areas associated with relatively large muscles, such as the lower back, should blades, hip and calves.

Figure 23A:
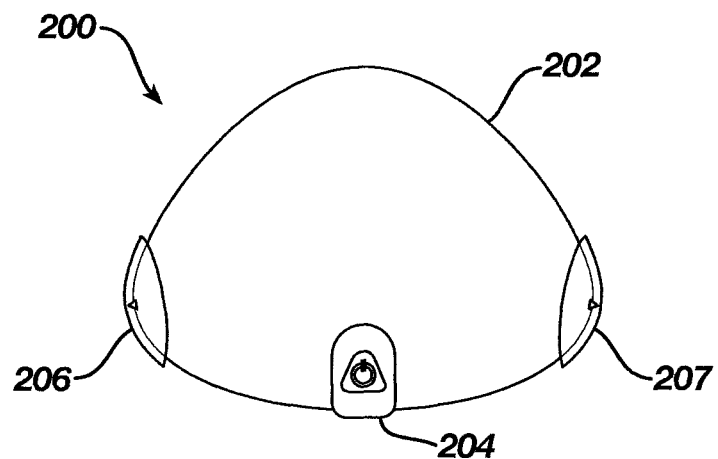
FIGS. 23A and 23B illustrate an exemplary embodiment of a flexible wearable therapeutic lamp platform according to an exemplary embodiment of this disclosure.
Figure 23B:
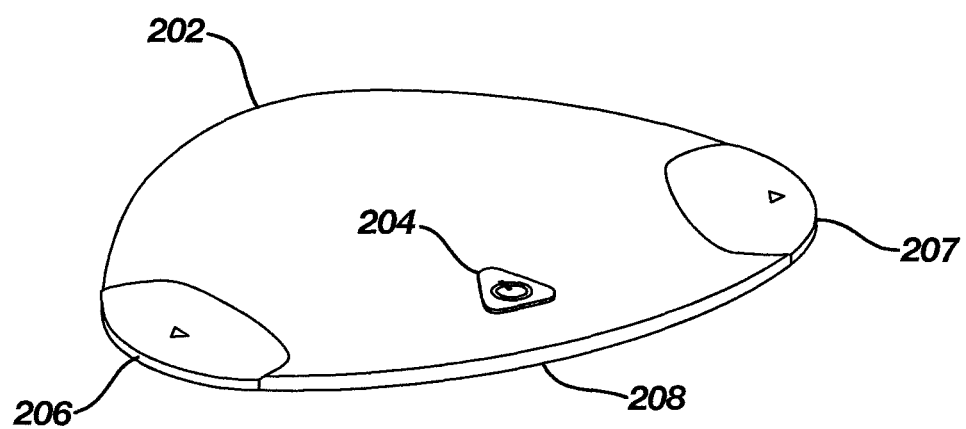

With reference to FIG. 23A, illustrated is a top view of the phototherapy device 200 and FIG. 23B is a perspective view of the phototherapy device 200, as seen by a user. As shown, the phototherapy device includes a flexible layer 202, handles 206 and 207 and a control bottom/removable Bluetooth controller housing to operate the phototherapy device. During operation, the phototherapy device 200 emits therapeutic radiation 208 to a user treatment area to relieve pain and/or provide therapeutic treatment for healing of the user treatment area.

Figure 24:
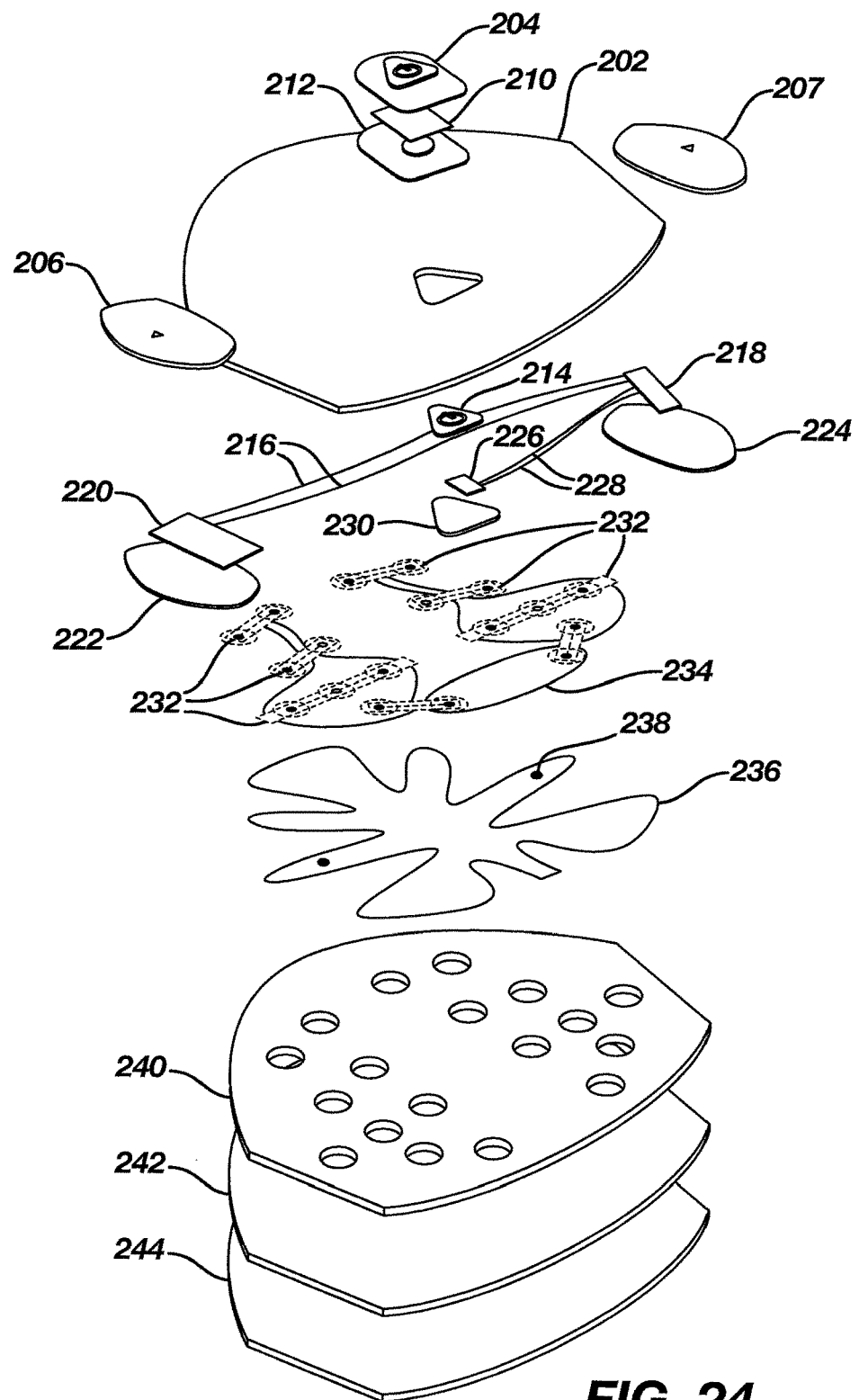
FIG. 24 is an exploded view of the flexible wearable therapeutic lamp platform illustrated in FIGS. 23A and 23B.

With reference to FIG. 24, illustrated is an exploded view of the flexible wearable phototherapy device shown in FIG. 23. As shown in FIG. 24, the phototherapy device 200 includes a control button/removable Bluetooth controller housing top 204 and bottom 230, a removable Bluetooth controller 210, an intermediate mounting board 212, handle tops 206 and 207, handle bottoms 222 and 224, ON/OFF button switch 214, wires 216 operatively connecting a battery 220 to a controller 218, wires 228 operatively connecting bottom switch 226 to controller 218, LED strips 232 operatively connected with wires 234, a heating component 236 including temperature sensors 238, a bendable/flexible bottom layer 240, a reflective layer 242 (note: LED clearance holes not shown) and a biomedical sticky gel 244.

Figure 25:
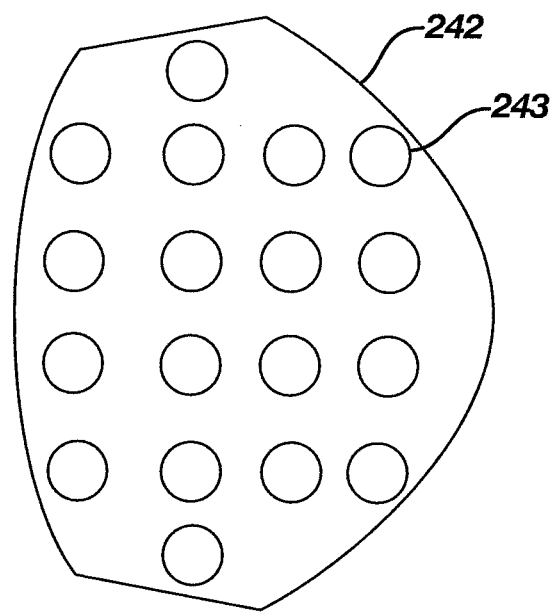
FIG. 25 is a plan view of the reflective layer as shown in FIG. 24, without the LED clearance holes shown.

With reference to FIG. 25, illustrated is a plan view of the reflective layer as shown in FIG. 24, with the LED clearance holes 243 shown.

Figure 26:
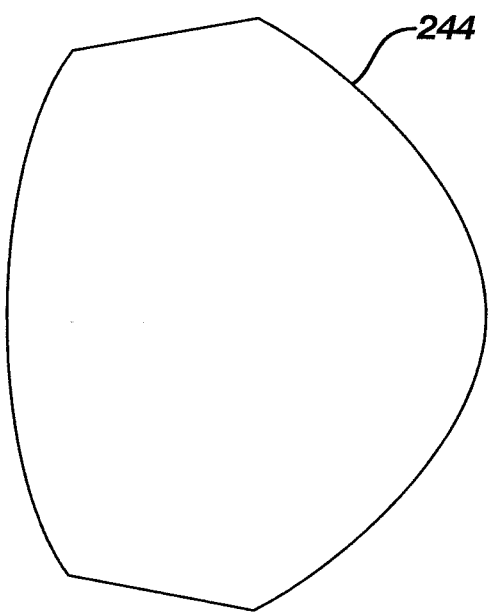
FIG. 26 is a plan view of the biocompatible sticky gel layer as shown in FIG. 24.

With reference to FIG. 26, illustrated is a plan view of the biocompatible sticky gel layer as shown in FIG. 24.

Figure 27:
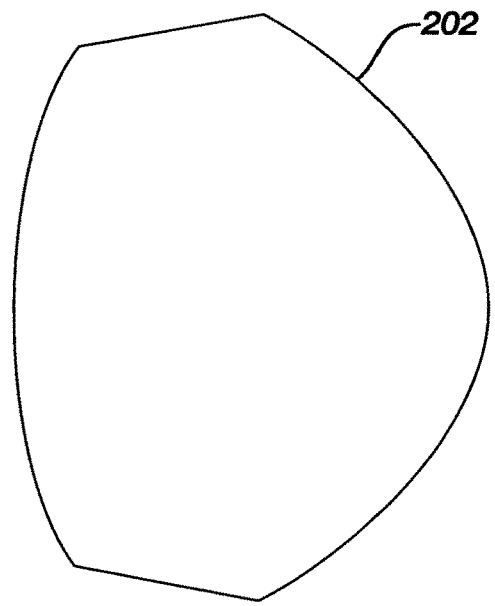
FIG. 27 is a plan view of the flexible layer as shown in FIG. 24.
Figure 28:
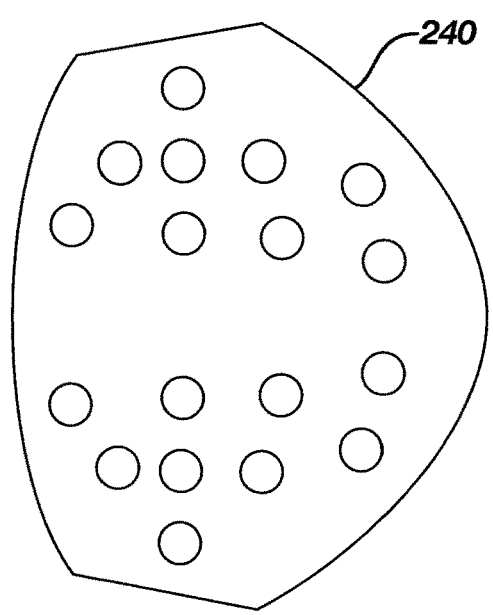
FIG. 28 is a plan view of the bendable bottom layer as shown in FIG. 24.

With reference to FIG. 27, illustrated is a plan view of the flexible layer as shown in 24, and 28 illustrates a plan view of the bendable bottom layer as shown in FIG. 24. Materials suitable for construction of these layers includes low durometer SAN, Neoprene, TPE, silicon, and fabric.

Figure 29:
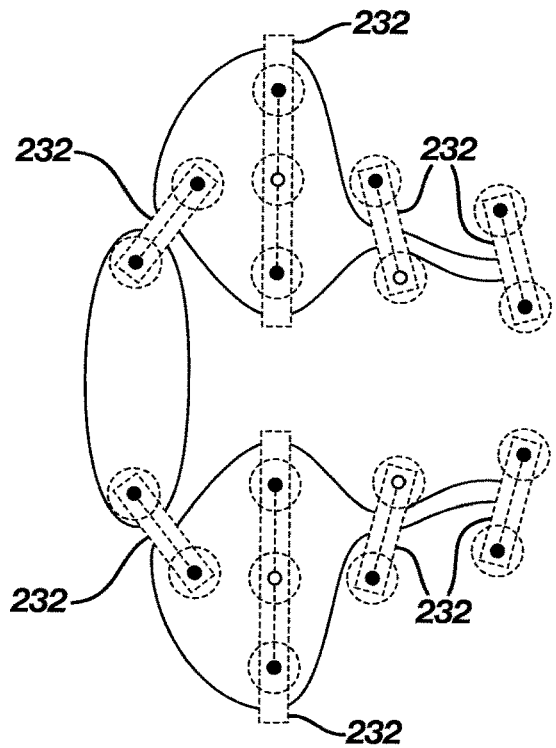
FIG. 29 shows a layout of LED strips according to an exemplary embodiment of this disclosure as shown in FIG. 14.

With reference to FIG. 29, shown is a layout of LED strips according to an exemplary embodiment of this disclosure as shown in FIG. 24.

Figure 30:
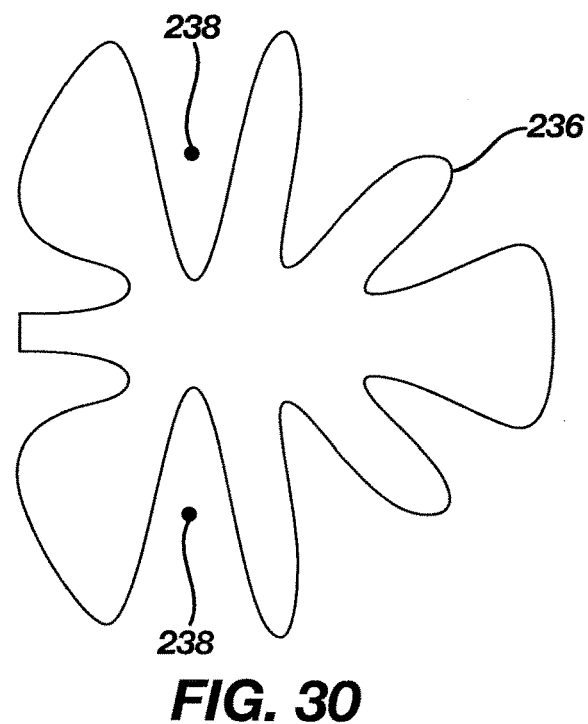
FIG. 30 is an enlarged detail view of the heating component and temperature sensor(s) arrangement as shown in FIG. 24.

With reference to FIG. 30, illustrated is an enlarged detail view of the optional heating component and temperature sensor(s) arrangement as shown in FIG. 24.

Figure 31:
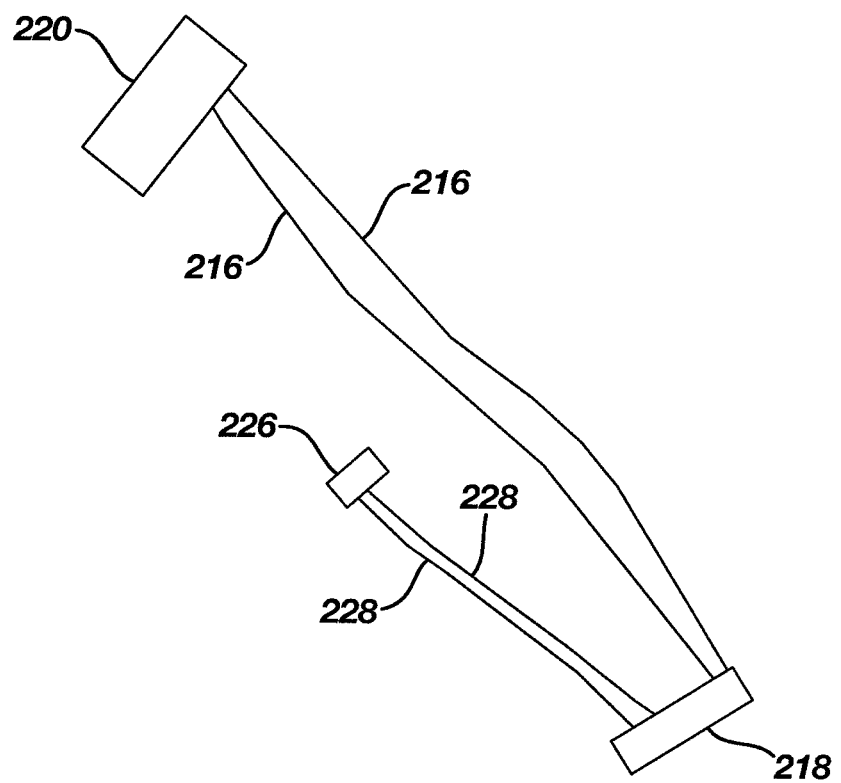
FIG. 31 is an enlarged detail view of the circuit board, i.e., controller, and the battery arrangement as shown in FIG. 24.

With reference to FIG. 31, illustrated is an enlarged detail view of the circuit board 218, i.e., controller separate power button optional Bluetooth antenna 226, and the battery arrangement 220 as shown in FIG. 24.

Figure 32:
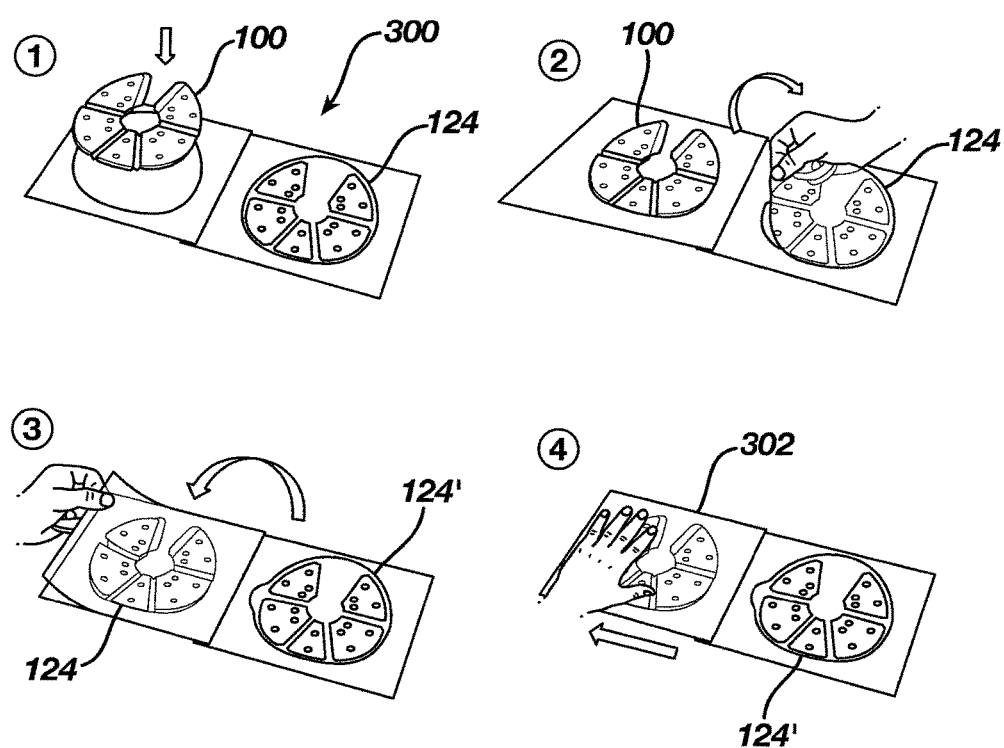
FIG. 32 shows a process to replace an adhesive layer on a wearable therapeutic lamp platform according to an exemplary embodiment of this disclosure.

With reference to FIG. 32, illustrated is a four step process to replace the biomedical sticky gel component of a phototherapy device 100 previously described.

After a user removes the used sticky gel component from the phototherapy device, the user initially places the phototherapy device bottom-side-up in the docking area of the carrier 300 shown.

Next, at step 2, the user removes an unused sticky gel component 124 from the carrier 300 and places the unused sticky gel component on the phototherapy device as shown in step 3.

Finally, the user applies pressure to the sticky gel component backing layer 302 to adhere the sticky gel component to the phototherapy device as shown at step 4.

Possible adhesive gel carrier designs include a boot package similar to a foldable travel case, roll type packaging where a user unrolls the package to remove the next adhesive gel, and a pencil case package.

Figure 33:
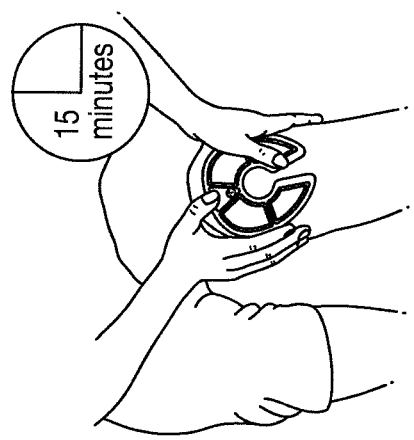
FIG. 33 shows a process to apply a wearable therapeutic lamp platform to a user treatment area according to an exemplary embodiment of this disclosure.
Figure 33:
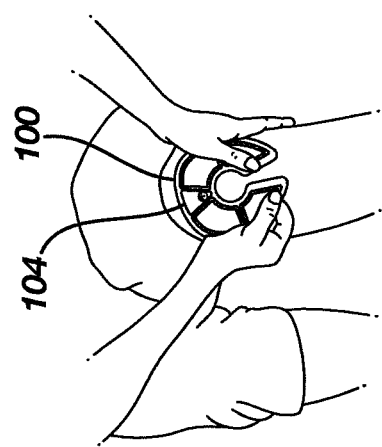
Figure 33:
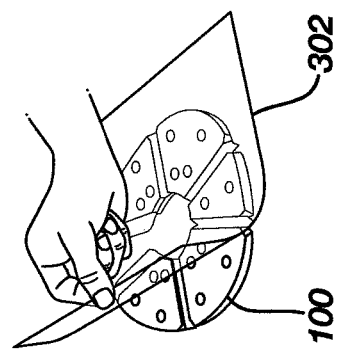

With reference to FIG. 33, shown is a process to apply the phototherapy device including a replaced sticky gel component to a user treatment area. Initially, the user removes the sticky gel replacement backing 302. Next, the user applies, with pressure, the phototherapy device 100 to a treatment area and activates the ON/OFF bottom switch 105 to begin a phototherapy treatment session, as shown in FIG. 34.

Figure 34A:
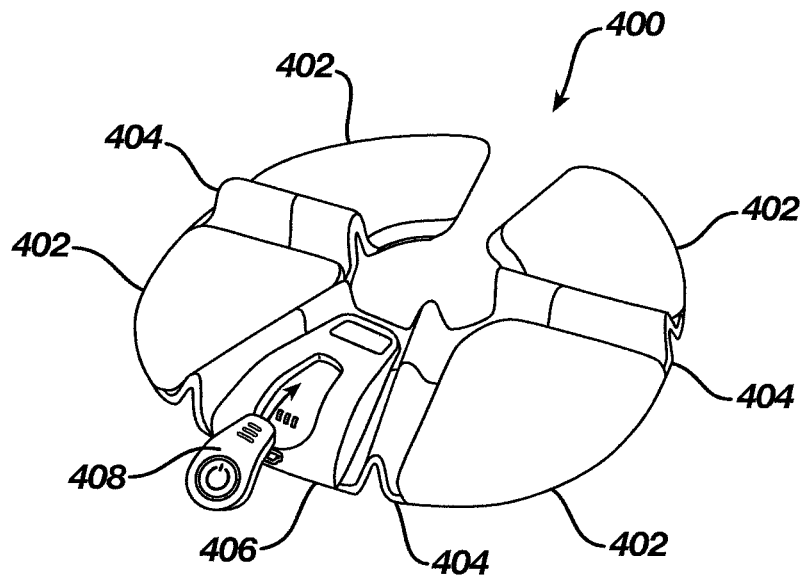
FIGS. 34A and 34B illustrate another stretchable wearable therapeutic lamp platform according to an exemplary embodiment of this disclosure; the therapeutic lamp platform including a SIM (Subscriber Identity Module) operatively connected to the platform.
Figure 34B:
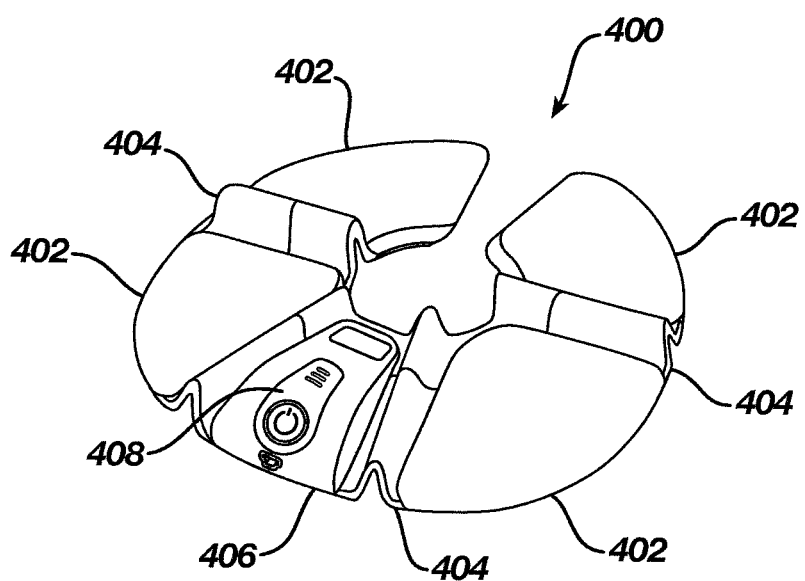

FIGS. 34A and 34B illustrate another stretchable wearable therapeutic lamp platform 400 according to an exemplary embodiment of this disclosure. The therapeutic lamp platform including a SIM (Subscriber Identity Module) operatively connected to the platform.

As shown, the phototherapy device 400 includes a plurality of soft surface pods 402, a plurality of expandable LED wire encasements 404, a controller 406 and a SIM Card device 408, which is used to activate the phototherapy device to provide a predetermined number of dosages of light therapy treatment, for example, 2-100 or any other number of dosages/sessions, including an unlimited number of treatments.

According to one exemplary embodiment, the SIM Card is a consumable product purchased by a user to provide a limited number of treatments before being required to purchase another SIM Card or electronically purchase the additional dosages for the depleted SIM Card.

Figure 35A:
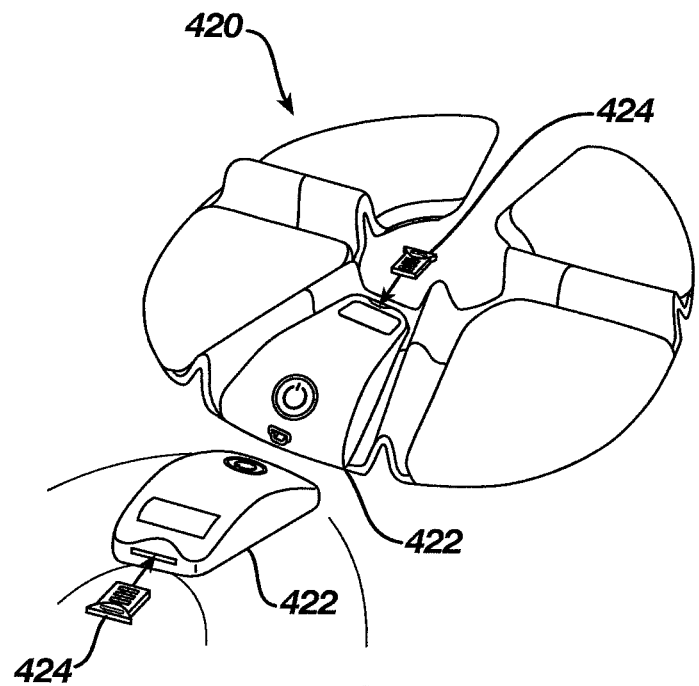
FIGS. 35A and 35B illustrate an exemplary embodiment of a wearable therapeutic lamp platform including a SIM top end card slot.
Figure 35B:
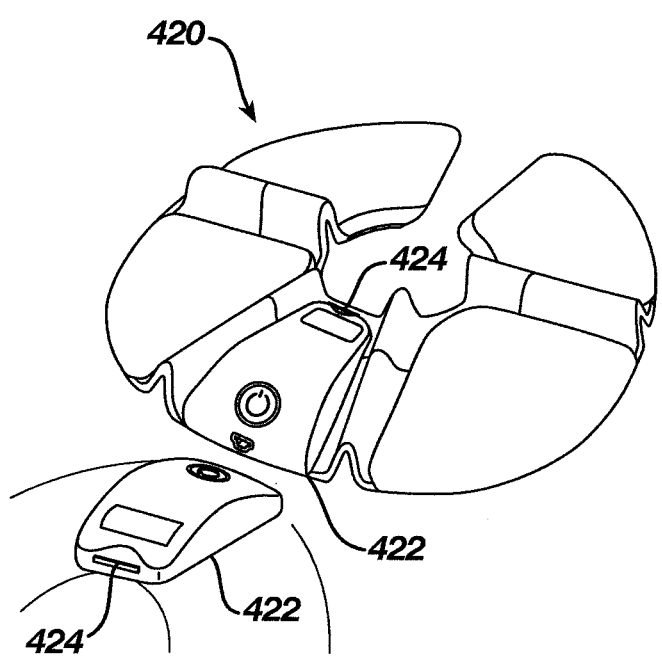

FIGS. 35A and 35B illustrate an exemplary embodiment of a wearable therapeutic lamp platform 420 including a SIM top end card slot 424 and controller 422.

Figure 36A:
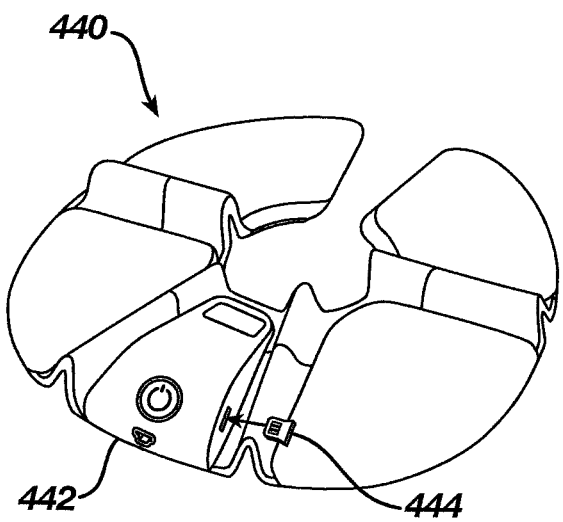
FIGS. 36A and 36B illustrate an exemplary embodiment of a wearable therapeutic lamp platform including a SIM side card slot.
Figure 36B:
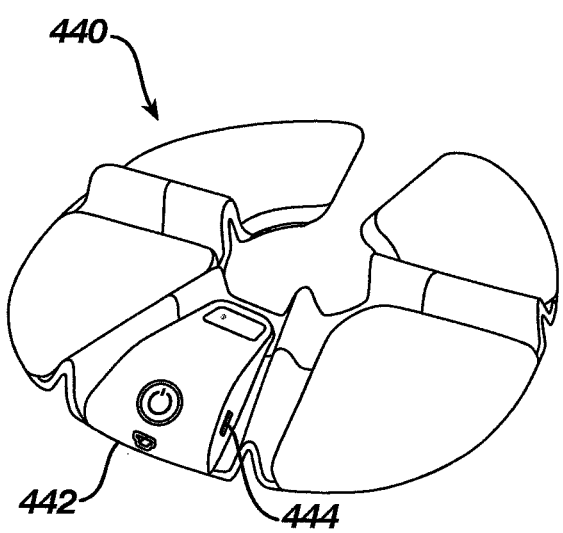

FIGS. 36A and 36B illustrate an exemplary embodiment of a wearable therapeutic lamp platform 440 including a SIM side card slot 444 and associated controller 442.

Figure 37A:
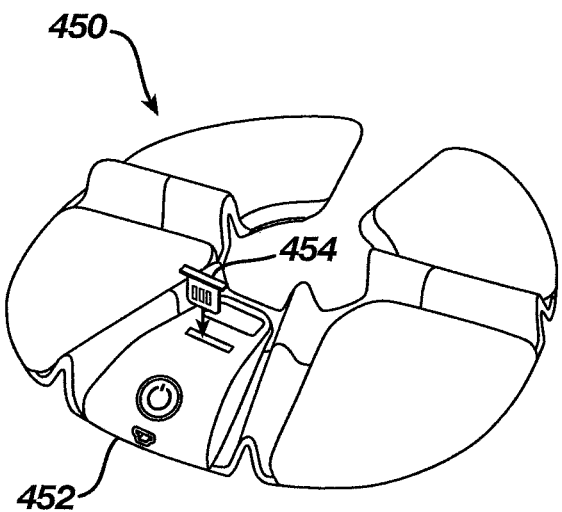
FIGS. 37A and 37B illustrate an exemplary embodiment of a wearable therapeutic lamp platform including a SIM retro video game card slot.
Figure 37B:
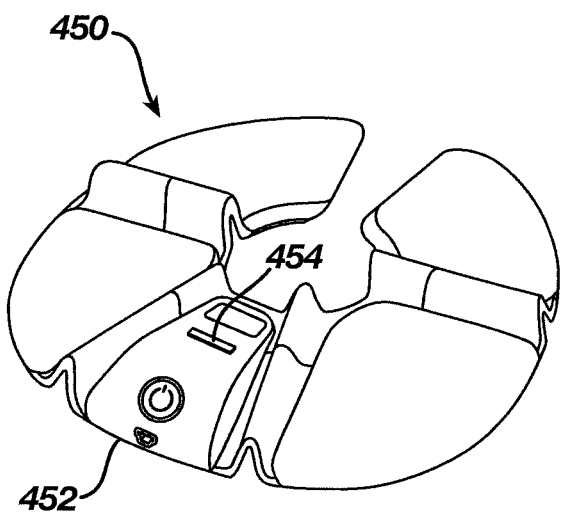

FIGS. 37A and 37B illustrate an exemplary embodiment of a wearable therapeutic lamp platform 450 including a SIM retro video game card slot 454 and associated controller 452.

Figure 38A:
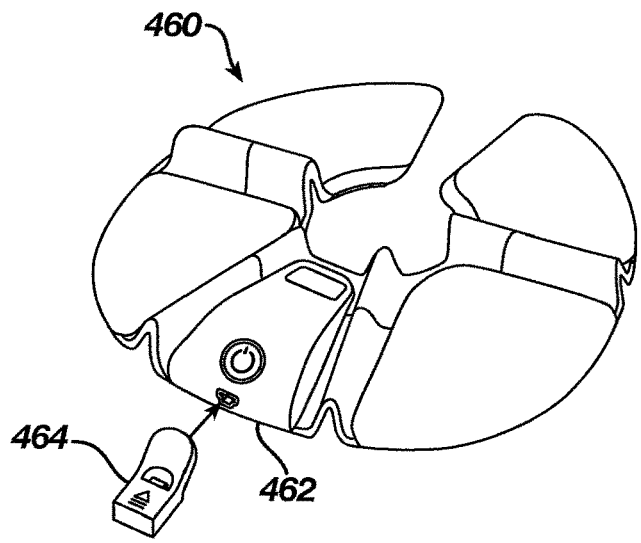
FIGS. 38A, 38B and 38C illustrate an exemplary embodiment of a wearable therapeutic lamp platform including a combination SIM and SIM card reader.
Figure 38B:
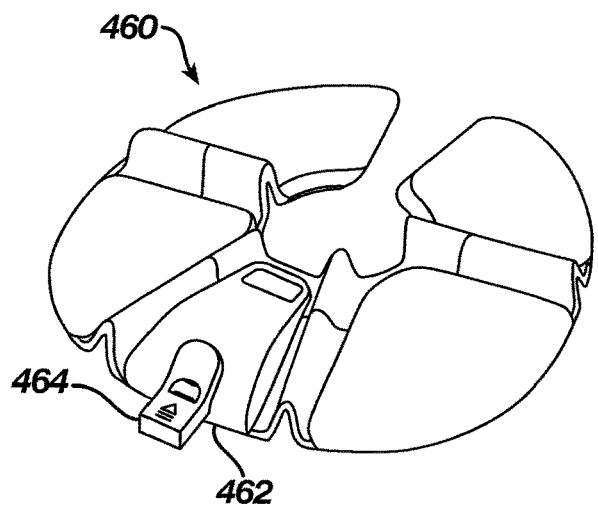
Figure 38C:
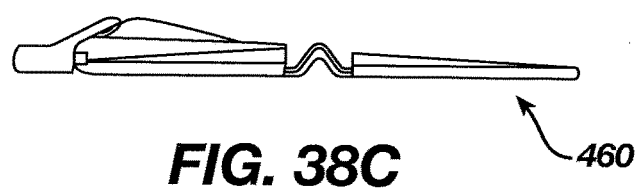

FIGS. 38A, 38B and 38C illustrate an exemplary embodiment of a wearable therapeutic lamp platform 460 including a combination SIM and SIM card reader 464 and associated controller 462.

Figure 39A:
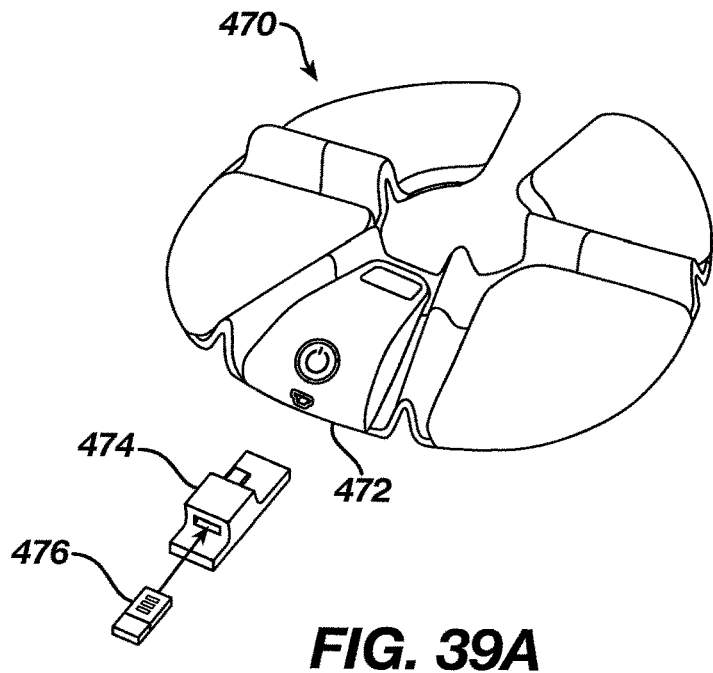
FIGS. 39A, 39B and 39C illustrate an exemplary embodiment of a wearable therapeutic lamp platform including a combination SIM and SIM card reader outside of the main pod.
Figure 39B:
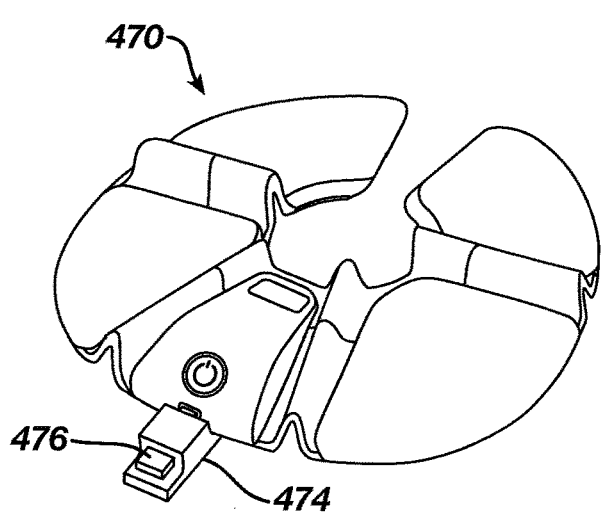
Figure 39C:
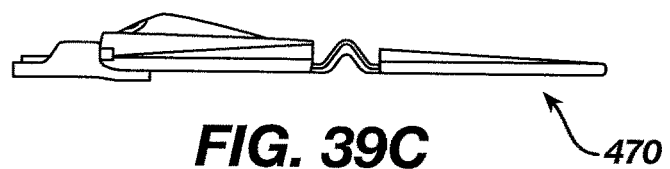

FIGS. 39A, 39B and 39C illustrate an exemplary embodiment of a wearable therapeutic lamp platform 470 including a combination SIM 476 and SIM card reader 474 outside of the main pod, and associated controller 472.

Figure 40A:
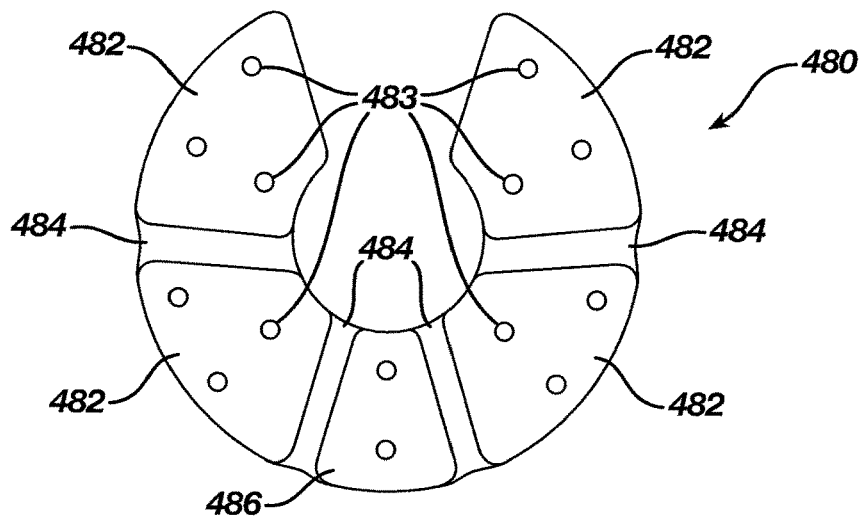
FIGS. 40A, 40B and 40C illustrate a stretchable wearable lamp platform according to an exemplary embodiment of this disclosure.
Figure 40B:
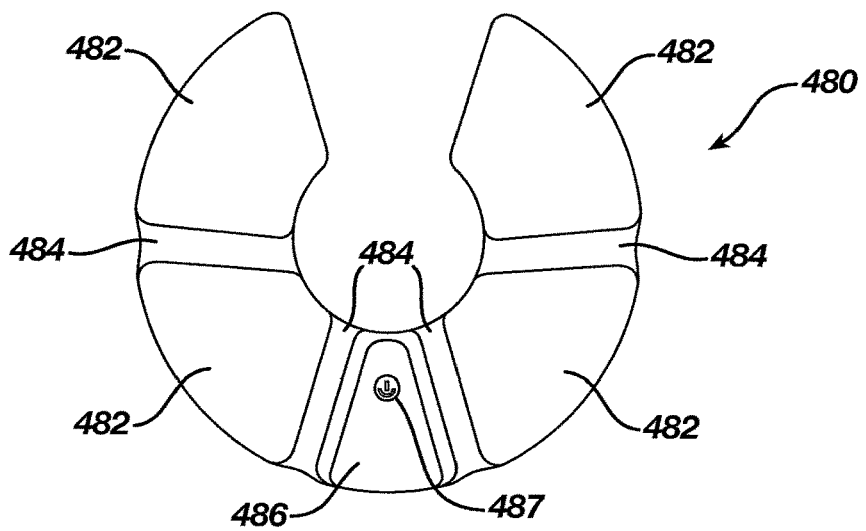
Figure 40C:
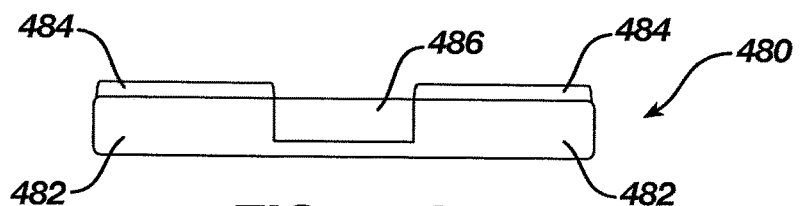

FIGS. 40A, 40B and 40C illustrate a stretchable wearable lamp platform according to an exemplary embodiment of this disclosure.

As shown, the phototherapy device 480 includes a plurality of soft surface pods 482 operatively interconnected by a plurality of expandable LED wire encasements 484 and a controller 486.

Figure 41:
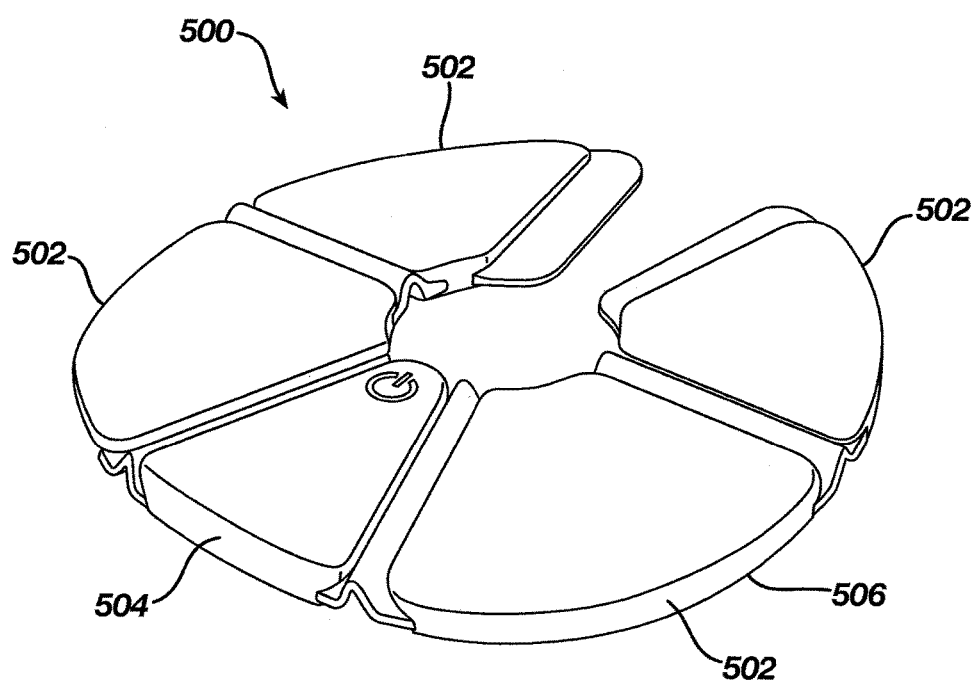
FIG. 41 is a perspective view of an exemplary embodiment of another stretchable wearable lamp platform according to this disclosure.

FIG. 41 is a perspective view of an exemplary embodiment of another stretchable wearable lamp platform 500 according to this disclosure.

As shown, the phototherapy device 500 includes a plurality of hard surface pods 502 and a controller pod 504, where the device emits therapeutic lamp radiation 506.

Figure 42:
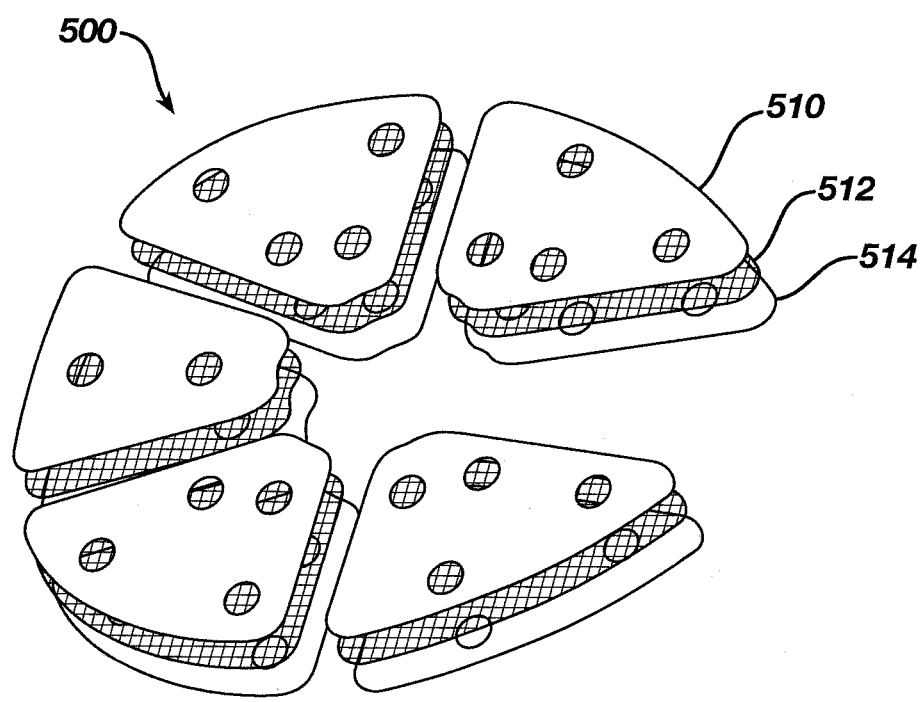
FIG. 42 illustrates the adhesive layer construction of the stretchable wearable lamp platform shown in FIG. 41.

FIG. 42 illustrates the adhesive layer construction 508 of the stretchable wearable lamp platform shown in FIG. 41.

As shown, the adhesive layer construction 508, i.e. sticky gel component, includes an adhesive layer 510 for attaching to the phototherapy device, a mid-layer structural layer 512 and an adhesive layer for the skin 514 of the user treatment area.

Figure 43A:
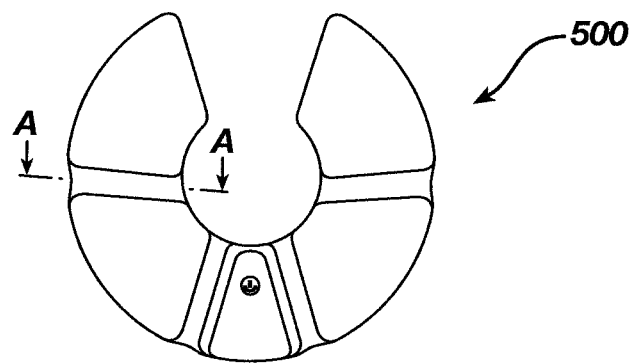
FIGS. 43A and 43B are detail views of the structural and electrical interconnection of the pods associated with the stretchable wearable lamp platform shown in FIG. 41.
Figure 43B:
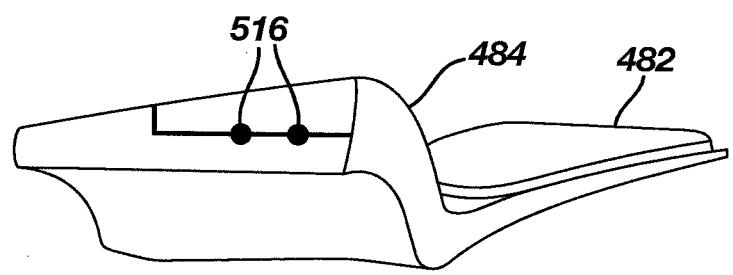

FIGS. 43A and 43B are detail views of the structural and electrical interconnection of the pods associated with the stretchable wearable lamp platform shown in FIG. 41.

As shown, the soft surface pod 482 is operatively connected to an expandable LED wire encasement 484 where the radial configuration provides for flexibility and stretchability of wires 516 which drive the LEDs.

Figure 44A:
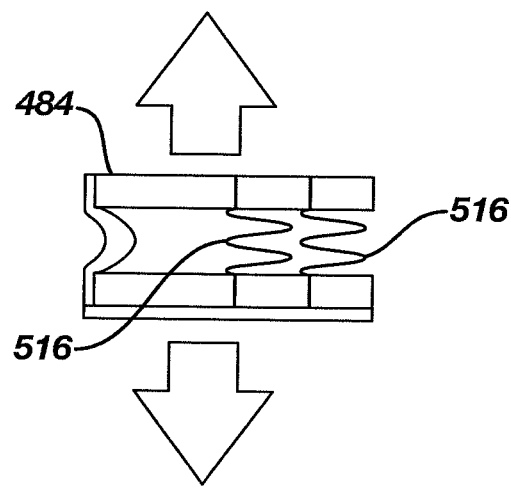
FIGS. 44A and 44B are additional detail views of the structural and electrical interconnections of the pods associated with the stretchable wearable lamp platform shown in FIG. 41.
Figure 44B:
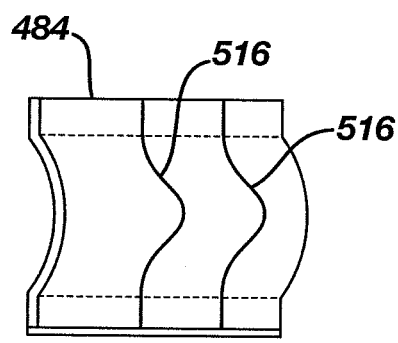

FIGS. 44A and 44B are additional detail views of the structural and electrical interconnections of the pods associated with the stretchable wearable lamp platform shown in FIG. 41, where FIG. 44A shows the wire encasement in a contracted form and FIG. 44B shows the wire encasement in an expanded form.

Figure 45A:
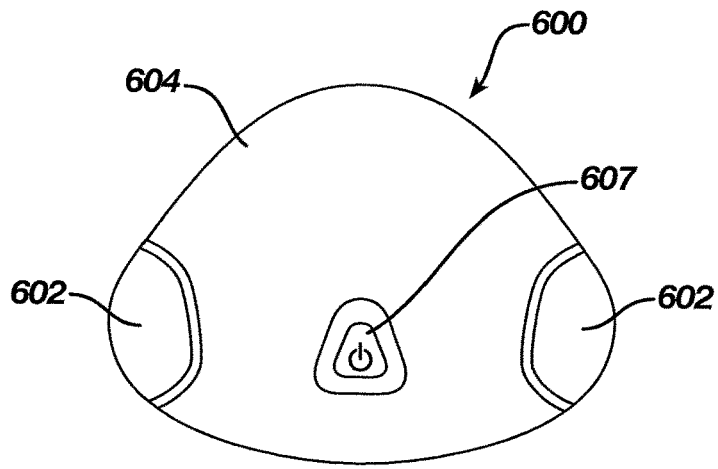
FIGS. 45A, 45B and 45C illustrate a flexible wearable lamp platform according to an exemplary embodiment of this disclosure.
Figure 45B:
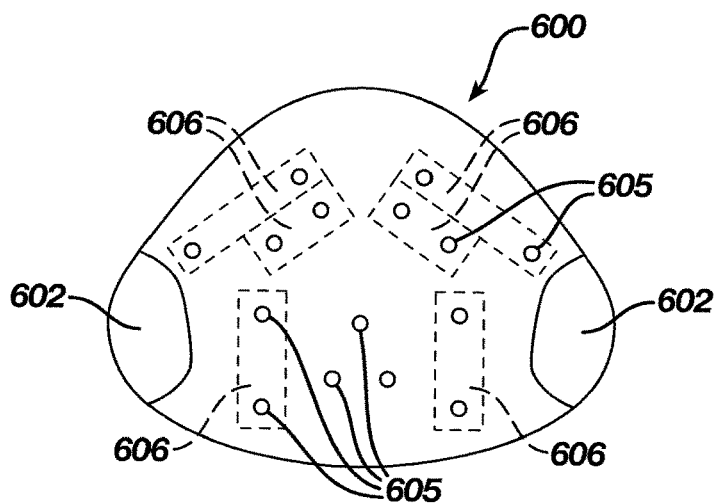
Figure 45C:
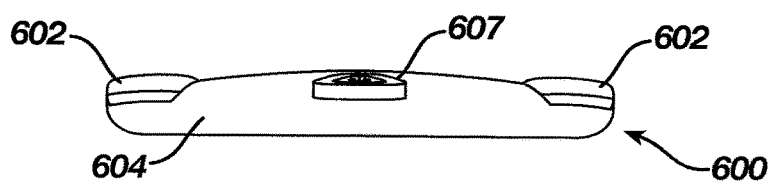

FIGS. 45A, 45B and 45C are illustrations of a flexible wearable lamp platform 600 according to an exemplary embodiment of this disclosure.

As shown, the phototherapy device 600 includes handles 602, a flexible stretchable layer 604, LED strips 606 and an ON/OFF control switch encasement.

Figure 46:
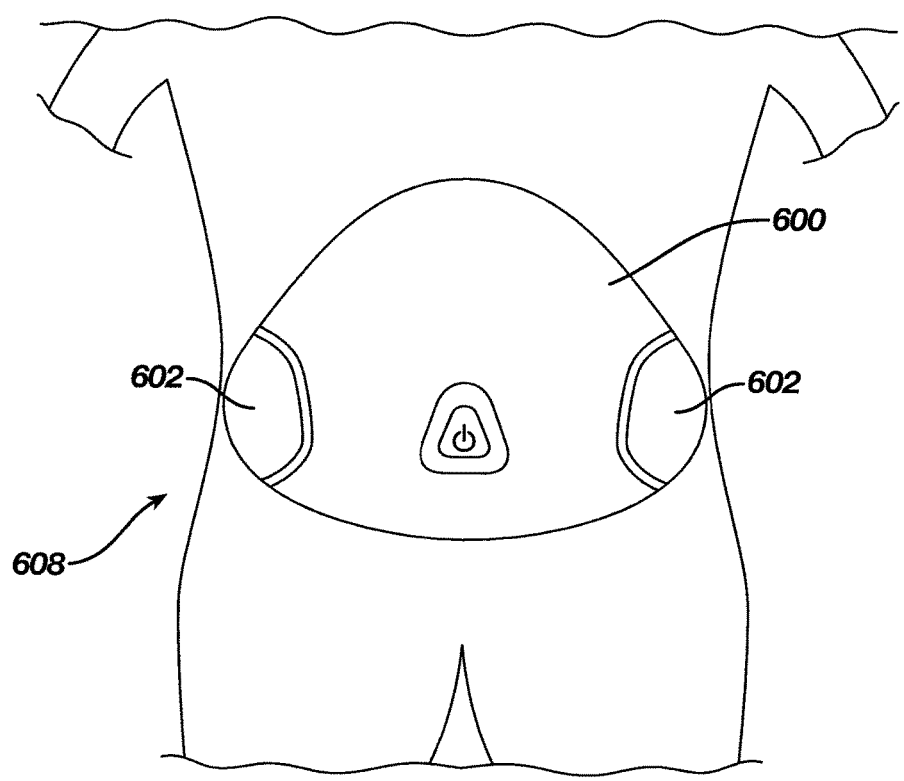
FIG. 46 illustrates the flexible wearable lamp platform shown in FIGS. 45A, 45B and 45C, applied to a user's lower back area.

FIG. 46 illustrates the flexible wearable lamp platform shown in FIGS. 45A, 45B and 45C, applied to a user's lower back area.

Figure 47:
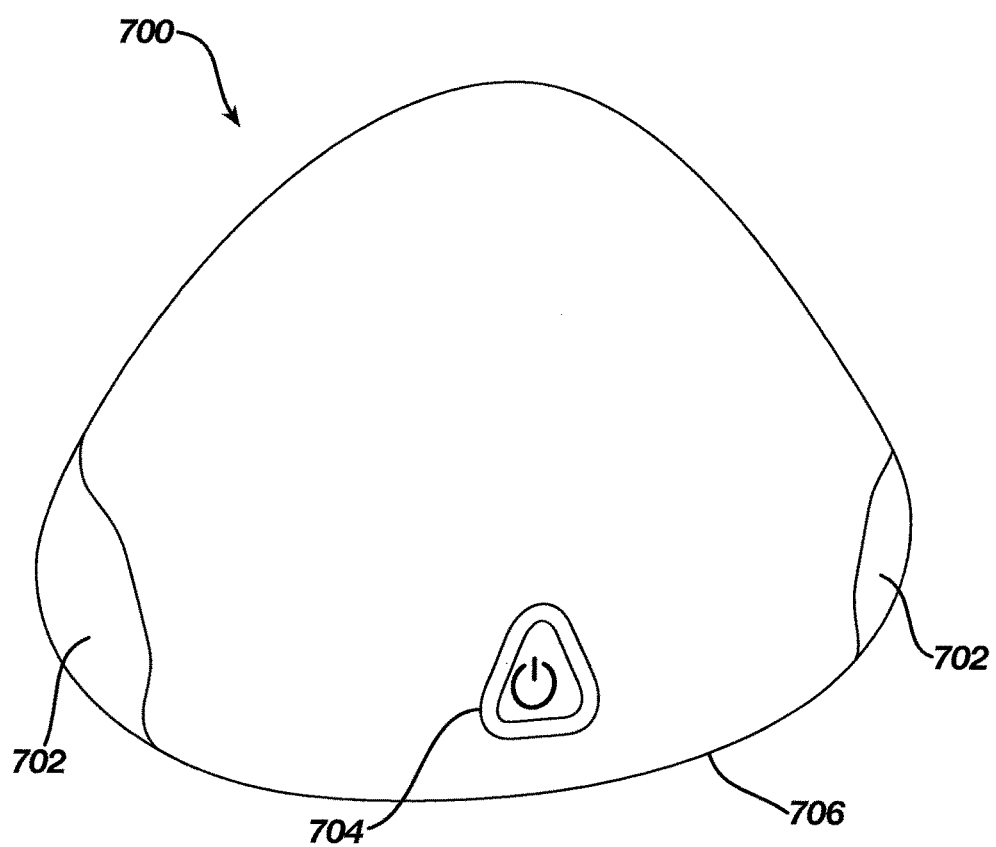
FIG. 47 illustrates a flexible wearable lamp platform according to an exemplary embodiment of this disclosure.

FIG. 47 illustrates another flexible wearable lamp platform 700 according to an exemplary embodiment of this disclosure, the platform 700 including handles 702, and an on/off control encasement 704, where the device provides therapeutic lamp radiation 706.

Figure 48:
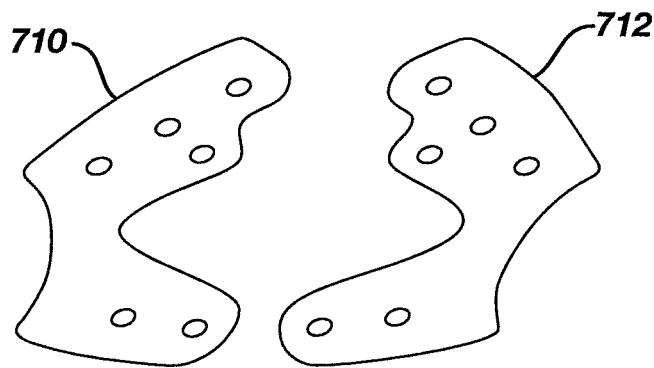
FIG. 48 illustrates an exemplary embodiment of the replaceable adhesive layers included in the flexible wearable lamp platform shown in FIG. 47.
Figure 49:
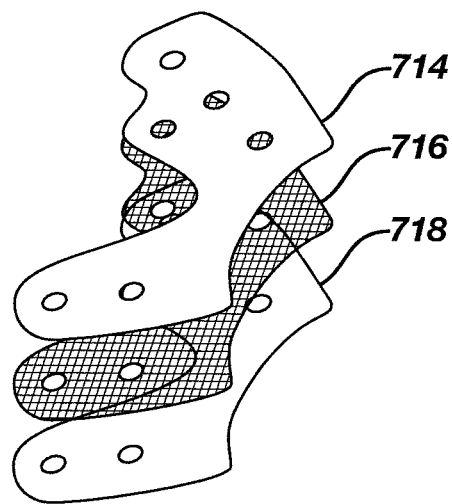
FIG. 49 illustrates the layered construction of the replaceable adhesive layers shown in FIG. 48.

FIG. 48 illustrates an exemplary embodiment of the replaceable adhesive layers included in the flexible wearable lamp platform shown in FIG. 47, and FIG. 49 illustrates the layered construction of the replaceable adhesive layers shown in FIG. 48.

As shown, included is a first adhesive pad portion 710 and a second adhesive pad portion 712. Adhesive pads 710 and 712 include an adhesive layer 714 to attach to the phototherapy device structure, a mid-layer structural component 716 and an adhesive layer 718 for attaching to the skin.

With reference to FIGS. 50A-50E, shown are flow charts of a control program to operate a flexible wearable therapeutic lamp platform according to an exemplary embodiment of this disclosure.

Figure 50A:
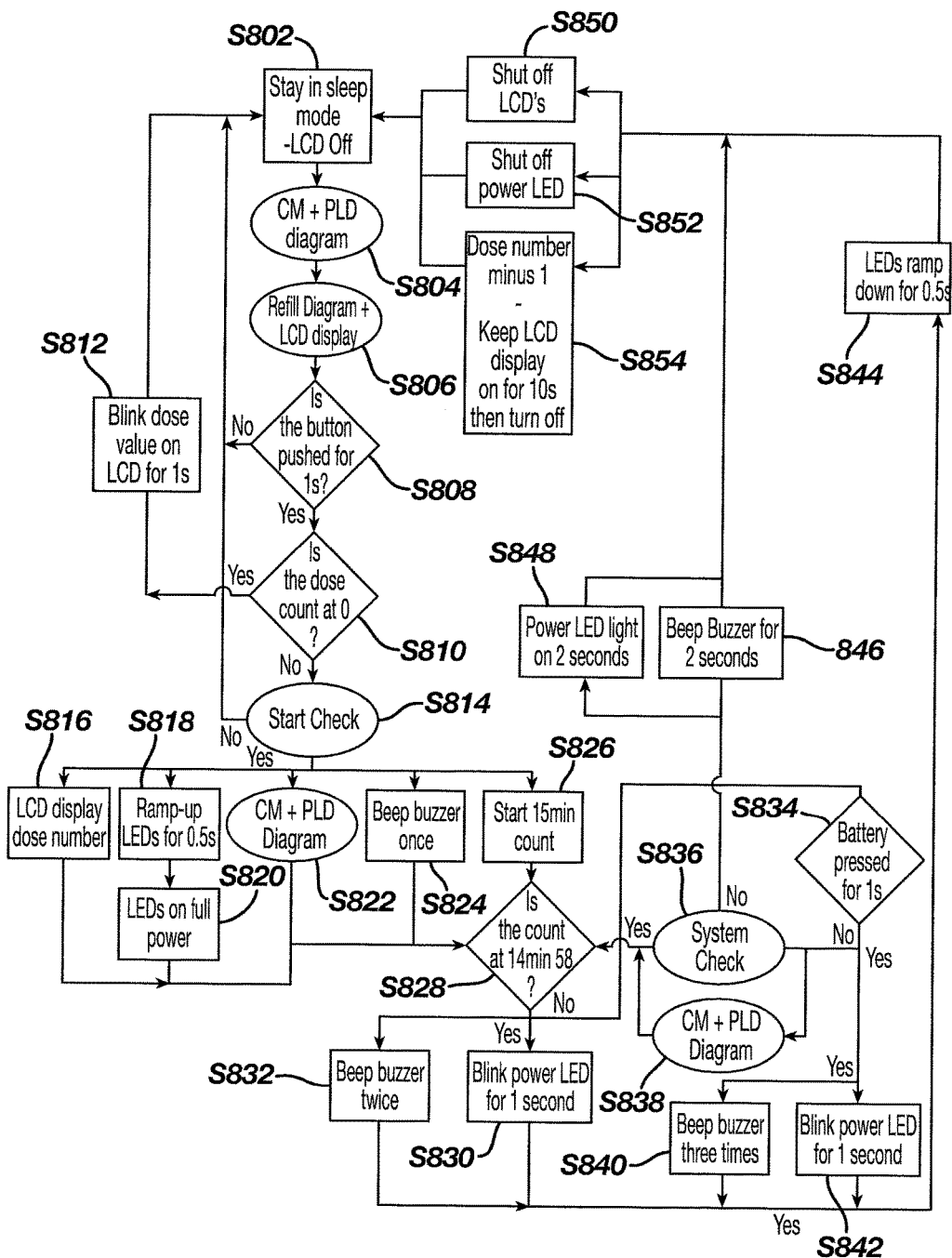
FIGS. 50A-50E are flow charts of a control program to operate a flexible wearable lamp platform according to an exemplary embodiment of this disclosure.

FIG. 50A is a flow chart of the main operational control program, which operates as follows:

Initially at step S802, the phototherapy device is under power and operates in a Sleep Mode with the LCD display off.

Figure 50B:
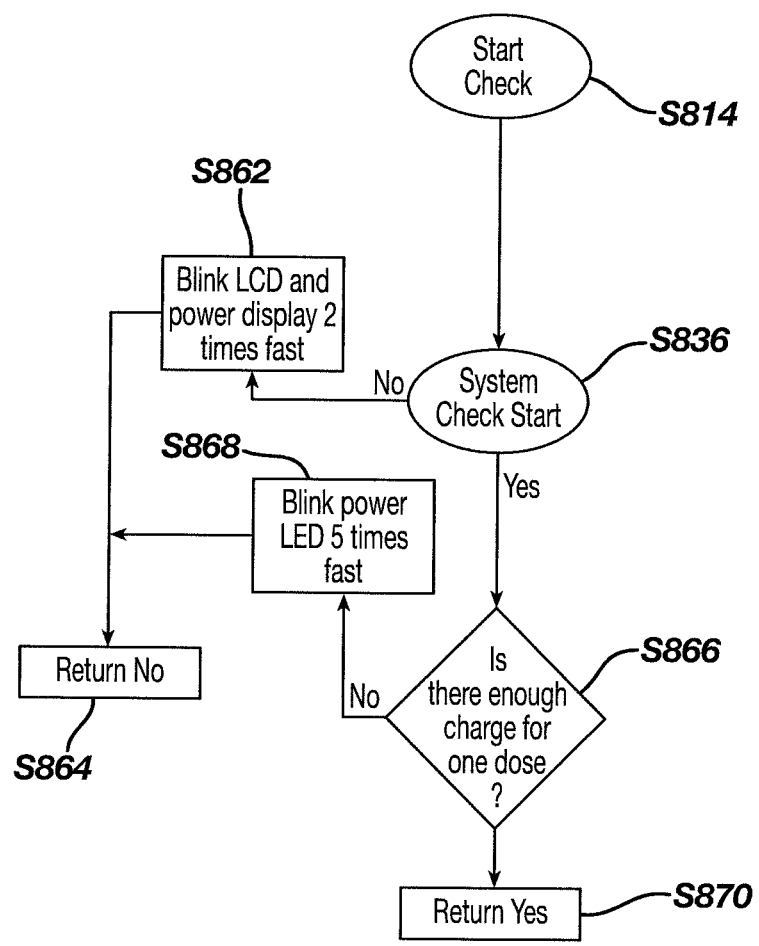
Figure 50C:
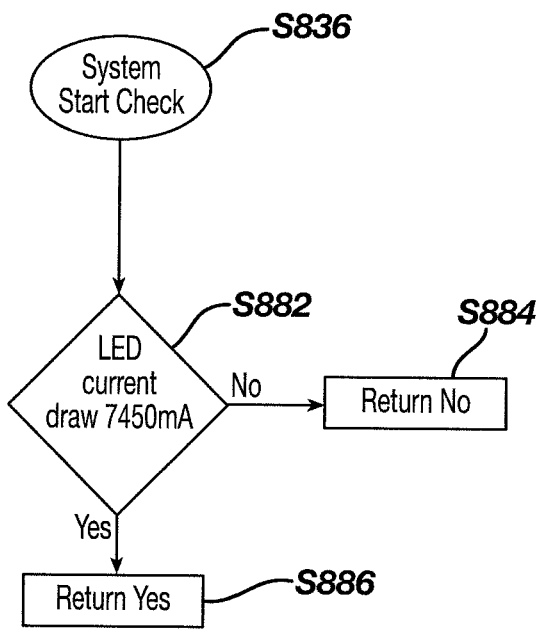
Figure 50D:
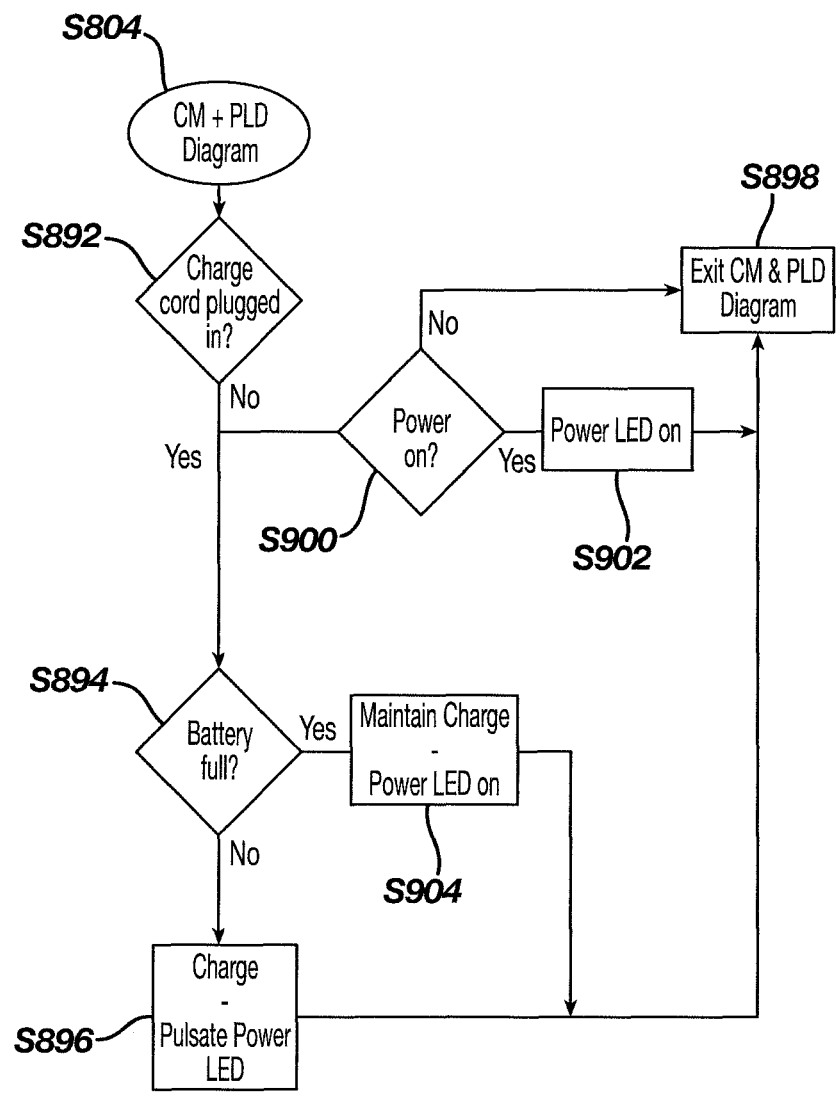

During Sleep Mode, the control program executes a CM & PLD (Charge Manager and Power LED Display) subcontrol program S804, as shown in FIG. 50D.

Figure 50E:
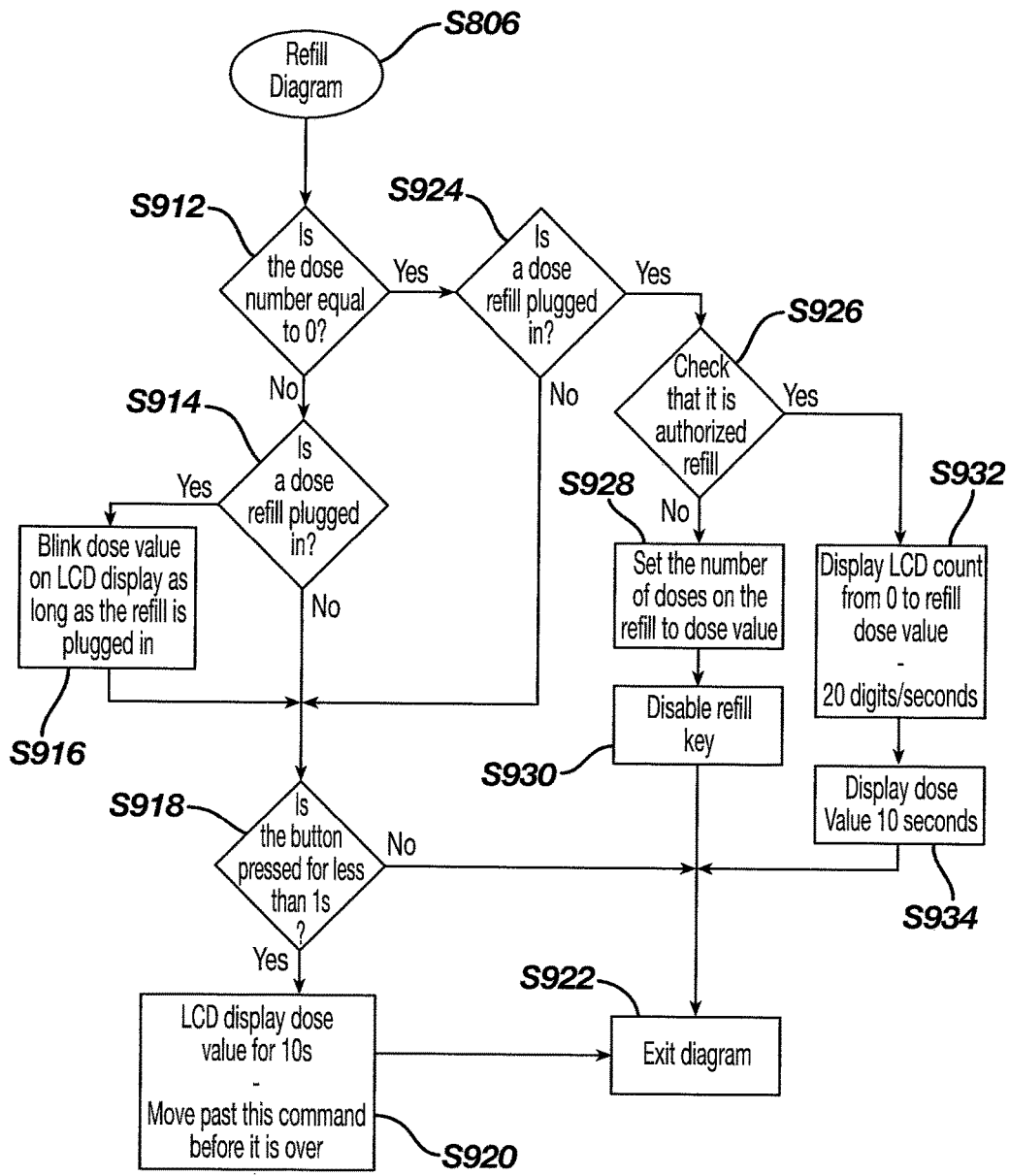

Next, the control program executes a Refill and LCD Display subcontrol program S806, as shown in FIG. 50E.

Next, at step S808, the control program monitors the control ON/OFF button to determine if the ON/OFF button is pushed for 1 second. If not, the control program returns to step S802. If yes, the control program next executes step S810 to determine if the device has remaining dosages available.

If the dosage counter is zero, then the control program executes step S812 and blinks the dose value of "0" on the LCD to notify the user that no dosages are available. If there are remaining dosages, the control program executes step S814 to perform a Start Check subcontrol as shown in FIG. 50B.

If the Start Check subcontrol program is not executed satisfactorily, the control program returns to step S802.

After the Start Check subcontrol program is executed successfully, the control program executes step S816 to display the dose number, step S818 and S820 to ramp-up the LED to full power in 0.5 seconds, executes CM & PLD subcontrol program S822, step S824 to beep the buzzer once, and step S826 to start a 15 minute dosage session counter.

Next, at step S828, the control program monitors the dosage session counter until the active dosage session is completed, at which time step S832 beeps the buzzer twice and, at step S830, LED power is blinked for 1 second S834, both steps S832 and S830 notifying the user the currently active dosage session has been completed.

Next, the control program executes step S844 to ramp down LED power in 0.5 seconds, then the control program executes step S850 to shut off the LEDs, step S852 to shut off power to the LEDs, and step S854 to display available number of doses to the user, which is one less than previously available and displayed at step S816.

Next, the control program reviews Sleep Mode at step S802.

If, at step S828, the control program has not yet reached the end of the current active dosage session, the control program executes step 834 to monitor the ON/OFF button state, where, if the ON/OFF button is not pressed for 1 second, the control program executes subcontrol program System Check at step S836 and subcontrol program CM & PLD control program at step S838 until the current active dosage session is completed.

In the event the user presses the ON/OFF button for 1 second during the dosage session, the control program terminates the current active dosage session by executing step S840 to beep the buzzer three times and step S842 to blink the LED power for 1 second, and then executes steps S844, S850, S852 and S854 as previously described.

FIG. 50B is a flow chart of the Start Check subcontrol program S814.

Initially, at step S836, the system Check Start subcontrol program S836 is executed and if not completed successfully, the subcontrol program performs step S862 to blink the LCD display and LED power to notify user at the failure, and returns to main program at step S864 indicating "NO" passage of Start Check.

After the successful completion of step S836, the subcontrol program executes step S866 to determine if there is enough battery power/charge to complete a phototherapy dose; if there is not, the subcontrol program blinks the LEDs 5 times fast to notify the user and returns to the main program at step S864.

FIG. 50C is a flow chart of the system Check Start subcontrol program S836.

The system Check Start subcontrol program monitors LED power draw at step S882 and after the LED power is greater than 450 mA, indicating a proper dosage radiant energy amount, the subcontrol program returns to the main program at S886 to continue executing the main control program to provide a dosage, otherwise a "NO" is returned at step S884 until adequate power is drawn by the LEDs.

FIG. 50D is a flow chart of the CM & PLD subcontrol program.

Initially, the subcontrol program S804 determines if the charge cord is plugged in at step S892. If the charge cord is not plugged in, step S900 is executed to determine if the power is ON, and, if it is, the LEDs are powered at step S902, and, at step S898, the CM & PLD subcontrol program is exited. If the power is determined to be OFF at step S900, the CM & PLD subcontrol program is exited at step S898.

If the charge cord is determined to be plugged in at S892, the subcontrol program determines at step S894 if the battery is fully charged. If YES, step S904 maintains charge and the power ON LED is illuminated and step S898 is performed to exit the CM & PLD subcontrol program. If the battery is determined to require charging at step S894, the subcontrol program executes step S896 to charge the battery while pulsating the power LED until the device is fully charged.

After completion of the battery charging step S896, the subcontrol program performs step S898 to exit the CM & PLD subcontrol program.

FIG. 50E is a flow chart of the Refill and LED display subcontrol program S806.

Initially, the subcontrol program determines if the dosage number is equal to 0. If it is equal, step S924 is executed to determine if a refill cartridge is plugged in the device. If no refill cartridge is available, the subcontrol program executes step S916 to blink the dose value on the display to notify the user a refill is required.

After step S924 determines a refill cartridge is available, step S926 determines if the refill cartridge is authorized. If the refill cartridge is not authorized, steps S928 and S930 are executed to disable the refill cartridge. If the refill cartridge is determined to be authorized, the subcontrol program executes step S932 to display the addition of the refill doses amount and step S934 displays the total number of available doses for 10 seconds to the user.

At step S918, the subcontrol program monitors the ON/OFF button and if the ON/OFF button is not pressed, the subcontrol program exits at step S922. If the ON/OFF button is pressed for 1 second, step S920 is executed to display on the LCD the dose value for 10 seconds and then performs step S922 to exit the subcontrol program.

Some portions of the detailed description herein are presented in terms of algorithms and symbolic representations of operations on data bits performed by conventional computer components, including a central processing unit (CPU), memory storage devices for the CPU, and connected display devices. These algorithmic descriptions and representations are the means used by those skilled in the data processing arts to most effectively convey the substance of their work to others skilled in the art. An algorithm is generally perceived as a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be understood, however, that all of these and similar terms are to be associated with the appropriate physical quantities and are merely convenient labels applied to these quantities. Unless specifically stated otherwise, as apparent from the discussion herein, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The exemplary embodiment also relates to an apparatus for performing the operations discussed herein. This apparatus may be specially constructed for the required purposes, or it may comprise a general-purpose computer selectively activated or reconfigured by a computer program stored in the computer. Such a computer program may be stored in a computer readable storage medium, such as, but is not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, and each coupled to a computer system bus.

The algorithms and displays presented herein are not inherently related to any particular computer or other apparatus. Various general-purpose systems may be used with programs in accordance with the teachings herein, or it may prove convenient to construct more specialized apparatus to perform the methods described herein. The structure for a variety of these systems is apparent from the description above. In addition, the exemplary embodiment is not described with reference to any particular programming language. It will be appreciated that a variety of programming languages may be used to implement the teachings of the exemplary embodiment as described herein.

A machine-readable medium includes any mechanism for storing or transmitting information in a form readable by a machine (e.g., a computer). For instance, a machine-readable medium includes read only memory ("ROM"); random access memory ("RAM"); magnetic disk storage media; optical storage media; flash memory devices; and electrical, optical, acoustical or other form of propagated signals (e.g., carrier waves, infrared signals, digital signals, etc.), just to mention a few examples.

The methods illustrated throughout the specification, may be implemented in a computer program product that may be executed on a computer. The computer program product may comprise a non-transitory computer-readable recording medium on which a control program is recorded, such as a disk, hard drive, or the like. Common forms of non-transitory computer-readable media include, for example, floppy disks, flexible disks, hard disks, magnetic tape, or any other magnetic storage medium, CD-ROM, DVD, or any other optical medium, a RAM, a PROM, an EPROM, a FLASH-EPROM, or other memory chip or cartridge, or any other tangible medium from which a computer can read and use.

Alternatively, the method may be implemented in transitory media, such as a transmittable carrier wave in which the control program is embodied as a data signal using transmission media, such as acoustic or light waves, such as those generated during radio wave and infrared data communications, and the like.

It will be appreciated that variants of the above-disclosed and other features and functions, or alternatives thereof, may be combined into many other different systems or applications. Various presently unforeseen or unanticipated alternatives, modifications, variations or improvements therein may be subsequently made by those skilled in the art which are also intended to be encompassed by the following claims.

What is claimed is:

1. A phototherapy device comprising: a wearable therapeutic lamp platform including:
   a plurality of radiant lamps configured to provide radiant energy to a user treatment area, the plurality of radiant lamps including a mixed combination of different wavelength energy;
   a control pod including a controller operatively connected to the plurality of radiant lamps and configured to control the plurality of radiant lamps;
   a flexible reflective layer including a top surface and a reflective bottom surface, the reflective layer including a plurality of radiant energy communication areas, each of the plurality of radiant energy communication areas directly aligned with a respective one of the plurality of radiant lamps located substantially near the top surface and disposed to communicate the radiant energy from the plurality of radiant lamps through the plurality of radiant energy communication areas and exiting the reflective bottom surface; and
   a replaceable flexible adhesive layer including a plurality of radiant energy communication areas, each of the adhesive layer plurality of radiant energy communication areas directly aligned with a respective one of the reflective layer plurality of radiant energy communication areas to communicate the radiant energy exiting the reflective bottom surface of the reflective layer through the adhesive layer plurality of radiant energy communication areas to the user treatment area, and the adhesive layer including a top surface and a bottom surface, the top surface adapted to be removably attached by a user to cover the reflective layer reflective bottom surface and the adhesive layer bottom surface adapted to be removably attached by the user to cover the user treatment area.

2. The phototherapy device according to claim 1, wherein the reflective layer radiant energy communication areas include apertures.

3. The phototherapy device according to claim 1, wherein the wearable therapeutic lamp platform is substantially U-shaped.

4. The phototherapy device according to claim 1, wherein the adhesive layer includes a sticky adhesive gel on one or both of the top surface and bottom surface.

5. The phototherapy device according to claim 1, wherein the adhesive layer includes a first sublayer made of a first sublayer material, a second sublayer made of a second material and a third sublayer made of a third sublayer material, the first sublayer adapted to be removably attached by the user to the reflective layer reflective bottom surface and attached to the second sublayer, the second sublayer attached to the first and third sublayer, and the first sublayer adapted to be removably attached to cover the user treatment area and attached to the second sublayer.

6. The phototherapy device according to claim 5, wherein the third sublayer includes one or more of a bioclusive material, a biocompatible material and an anti-microbial material.

7. The phototherapy device according to claim 1, wherein the plurality of radiant lamps include one or both of Red and Infrared wavelength radiant energy.

8. The phototherapy device according to claim 1, further comprising:
   one or more integrated and wearable batteries.

9. The flexible wearable device according to claim 8, wherein one or more of the reflective layer and adhesive layer is a silicon and/or urethane based material.

10. A flexible wearable phototherapy device comprising:
    a plurality of pods, each pod including a respective bottom surface, a plurality of radiant lamps including a mixed combination of different wavelength energy and one or more radiant lamp wires operatively connected to the plurality of radiant lamps, one of the plurality of pods configured as a control pod including a controller operatively connected to the radiant lamp wires and configured to control the plurality of radiant lamps of each of the plurality of pods, and each pod communicating radiant energy from the plurality of radiant lamps through the respective bottom surface to a user treatment area; and
    a plurality of radial flexible radiant lamp wire encasements operatively connecting each of the plurality of pods to one or more other pods to substantially and collectively conform the bottom surface of each pod to a contour of the user treatment area, each of the plurality of radiant lamp wire encasements independently, structurally and electrically connecting one or more adjacent pods and each of the plurality of radiant lamp wire encasements independently radially flexing relative to the connected one or more adjacent pods.

11. The flexible wearable phototherapy device according to claim 10, wherein one of the control pod and the other pods includes a power source to operatively power the plurality of radiant lamps associated with each of the plurality of pods.

12. The flexible wearable phototherapy device according to claim 10, further comprising:
a flexible reflective wall including a plurality of radiant energy communication areas aligned with the plurality of radiant lamps and disposed to communicate the radiant energy to the user treatment area.

13. The flexible wearable phototherapy device according to claim 10, further comprising:
a flexible adhesive layer including a first surface and a second surface, the first surface removably attached to the reflective layer bottom surface and the second surface adapted to removably attach the wearable phototherapy device and the second surface to the user treatment area.

14. The flexible wearable phototherapy device according to claim 10, wherein the plurality of radiant lamps include one or both of Red and Infrared wavelength radiant energy.

15. The flexible wearable phototherapy device according to claim 13, wherein the adhesive layer is a silicon and/or urethane based material.

16. The flexible wearable phototherapy device according to claim 10, wherein the plurality of radiant lamps are LEDs.

17. The phototherapy device according to claim 1, wherein the flexible adhesive layer radiant energy communication areas include apertures.

* * * * *